(12) United States Patent
Menkes et al.

(10) Patent No.: US 6,201,982 B1
(45) Date of Patent: Mar. 13, 2001

(54) QUICK-PLACEMENT ELECTROENCEPHALOGRAM (EEG) ELECTRODE

(75) Inventors: Alex Menkes; John R. Sakers, both of Baltimore, MD (US)

(73) Assignee: Baltimore Biomedical, Inc., Baltimore, MD (US)

( * ) Notice: Subject to any disclaimer, the term of this patent is extended or adjusted under 35 U.S.C. 154(b) by 0 days.

(21) Appl. No.: 09/346,694

(22) Filed: Jul. 2, 1999

Related U.S. Application Data

(60) Provisional application No. 60/091,681, filed on Jul. 2, 1998.

(51) Int. Cl.[7] ................................................. A61B 5/0478
(52) U.S. Cl. ............................................ 600/386; 600/383
(58) Field of Search ..................................... 600/382, 383, 600/386; 607/115, 149, 139, 79

(56) References Cited

U.S. PATENT DOCUMENTS

| | | | |
|---|---|---|---|
| 3,469,577 | * | 9/1969 | Kater ........................................ 600/386 |
| 3,896,790 | * | 7/1975 | Dikman ..................................... 600/386 |
| 4,067,321 | * | 1/1978 | Oda et al. ................................. 600/386 |
| 4,632,120 | * | 12/1986 | Sherwin et al. .......................... 600/386 |
| 4,709,702 | * | 12/1987 | Sherwin ..................................... 600/386 |
| 4,936,306 | * | 6/1990 | Doty ........................................... 600/386 |
| 5,222,498 | * | 6/1993 | Neward ...................................... 600/386 |

FOREIGN PATENT DOCUMENTS

405026909 * 10/1993 (JP) ................................ A61B/5/0408

* cited by examiner

Primary Examiner—Jeffrey R. Jastrzab
(74) Attorney, Agent, or Firm—Dorsey & Whitney LLP

(57) ABSTRACT

This invention provides a quick-placement EEG electrode. The EEG electrode is fixed to a patient's head by a first element or fixed section and a second element or movable section that operates in conjunction with the fixed section to trap hair and hold the EEG electrode in place. The EEG electrode contains a sponge that when compressed, dispenses electrolytic gel, acts as a shock absorber, and maintains contact with the scalp. The EEG electrode has a quick release mechanism with a break-away ring and locking groove for easy removal of the EEG electrode from the patient's scalp.

45 Claims, 30 Drawing Sheets

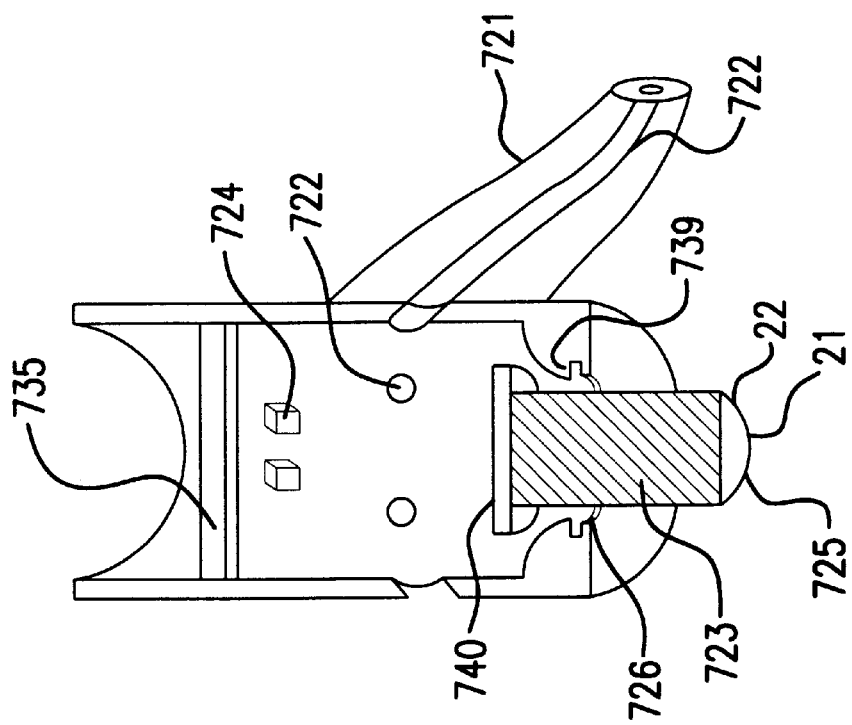
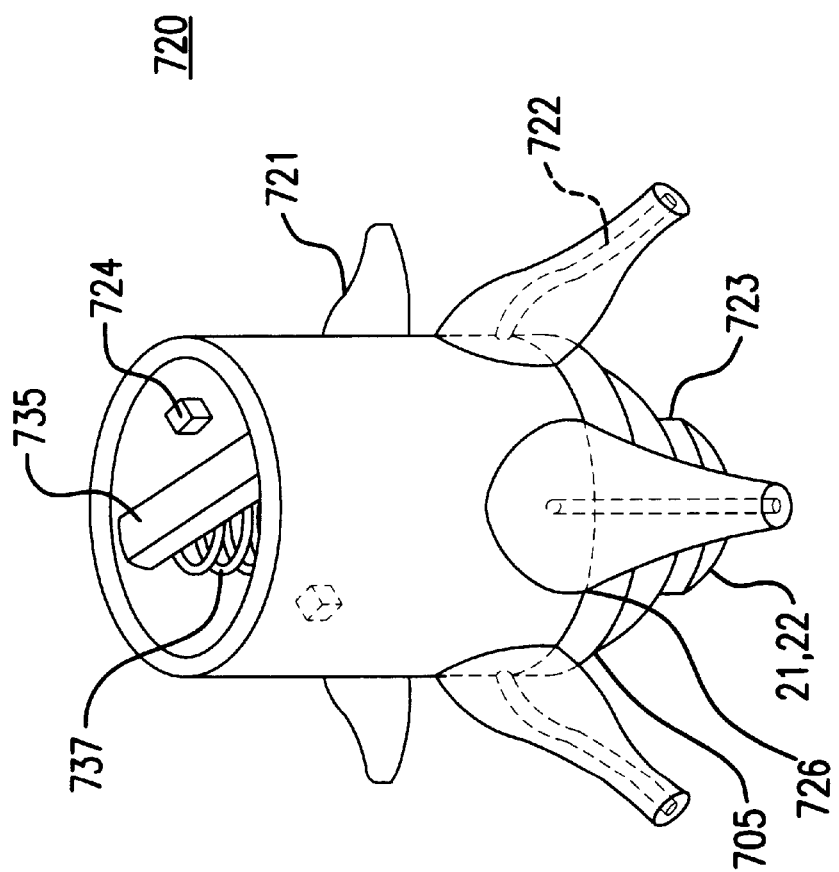
FIG.28b
FIG.28a

QUICK-PLACEMENT ELECTROENCEPHALOGRAM (EEG) ELECTRODE

This non-provisional application claims the benefit of provisional application U.S. serial No. 60/091,681 filed Jul. 2, 1998. The provisional application is hereby incorporated by reference.

STATEMENT REGARDING FEDERALLY SPONSORED RESEARCH OR DEVELOPMENT

This invention was made with government support under grant number 1R43MH59444 awarded by National Institute of Health. The government has certain rights in the invention.

TECHNICAL FIELD

This invention relates to electroencephalogram (EEG) electrodes. More particularly, the invention relates to EEG electrodes that can be quickly applied and removed from a patient's scalp. The invention also relates to methods for quickly and easily applying and removing the EEG electrode from the patient's scalp.

BACKGROUND ART

Attachment devices exist for fixing EEG electrodes to a patient's scalp. These devices may use colloidal glue, adhesive tape or bandages. EEG electrodes may also be attached by incorporating them into web matrix helmets. Placing and removing these EEG electrodes from a patient's scalp is time consuming. The EEG electrodes are uncomfortable to wear and may loose signal contact during extended ambulatory monitoring.

Web matrix helmets are headpieces made of a webbing material. Web matrix helmets are fastened to the patient's head by means of a chin strap and/or a neck strap with scalp-pattern electrodes attached along the under-surface of the web material. Web matrix helmets cannot be used unobtrusively in ambulatory settings. Furthermore, each contact area on the patient's head must be thickly coated with an electrolytic gel to obtain good signal quality. Even with this preparation, since the electrodes themselves trap large quantities of hair between the electrode body and the scalp, there is a possibility for signal loss from any one electrode. Also, during the course of long-term monitoring, re-application of electrolytic gel is often necessary to maintain signal quality. Lastly, web matrix helmets do not fit all head shapes and sizes, making electrode placements problematic with some patients.

Scalp placement electrodes may also be attached to the patient by means of an adhesive paste. The electrode is pressed into a large amount of electrolytic adhesive paste or gel applied at the desired placement site, and then the electrode is taped in place to allow the adhesive to set. The electrodes are obtrusive, and a large amount of electrolytic gel is needed to maintain proper contact because the electrode-scalp interface tends to dry out through evaporation. In addition, adhesive-attached scalp electrodes cannot be used in most ambulatory settings because they tend to become dislodged during normal movement or activity. Finally, this type of placement entails a messy and time consuming clean-up.

Colloidal glues achieve stronger bonding between the electrode and the scalp, but their use is both time and labor intensive. In a typical application, electrolytic gel is applied to the patient's scalp, the electrode is seated and taped in place, and the colloidal glue is applied and allowed to dry. This process can take 7–15 minutes per electrode. Removing the electrode requires applying a solvent, and the patient is inconvenienced because the collodion remains in the hair. In addition, the collodion and solvents emit strong fumes, limiting their use to specially ventilated rooms. Also, because the collodion can bond to unintended surfaces, special care must be used not to touch any other material while gluing the electrodes in place. Lastly, many patients may experience scalp irritation due to sensitivity or allergic reactions to the collodion.

SUMMARY OF THE INVENTION

This invention is directed to a quick-placement electroencephalogram (EEG) electrode that may be used for monitoring brain wave activity, for example. The quick-placement EEG electrode includes a first element or fixed section which is coupled to a second element or movable section. The movable section may be constructed of two pieces, such as a plunger and a grabbing element, for example. When the quick-placement EEG electrode is assembled, the plunger contacts the grabbing element. Alternately, the movable section may be molded as a single piece capable of functioning as both a plunger and a grabbing element. In both arrangements, the plunger penetrates a center opening of the fixed section, or cap. Downward pressure applied to the plunger causes the grabbing element to activate. In another arrangement, the fixed and movable sections include a cap and a coil spring.

The quick-placement EEG electrode is designed to clamp to a patient's hair by trapping hair between the first element and the second element. Alternatively, the patient's hair is trapped in the grabbing element alone. In another arrangement, the patient's hair is trapped with downward pressure on the movable section or plunger. A sponge carried in the movable section and containing electrolytic gel is compressed by the downward pressure on the plunger, causing release of the gel at the scalp contact point. The compressed sponge counters the downward force exerted on the trapped hair, acts as a shock absorber, and maintains constant contact between the scalp and the electrode. Finally, the quick-placement EEG electrode is easily removed by pushing down on the plunger or otherwise releasing the grabbing element.

The quick-placement EEG electrode maximizes the accuracy of EEG readings and exploits specific characteristics of electrolytic gel-type electrodes for long term monitoring. Dissipation of the gel from movement (friction) is minimized because the EEG electrode is held securely in place by gripping the base of the patient's hair. In addition, the EEG electrode design provides a covering for the cavity mounted sponge saturated with electrolytic gel. This covering traps the electrolytic gel between the EEG electrode and the scalp, thus minimizing evaporation and allowing the gel to remain stable over a longer time. Because it is attached to the hair, the quick-placement EEG electrode may be quickly applied and removed. Moreover, low visibility of the EEG electrode makes it more practical for long-term ambulatory monitoring.

BRIEF DESCRIPTION OF THE DRAWINGS

The invention is described with reference to the following drawings wherein like numerals refer to like elements, and wherein:

FIGS. 28a and 28b are a perspective and a cut-away view, respectively, of another embodiment of the EEG electrode;

DETAILED DESCRIPTION OF PREFERRED EMBODIMENTS

EEG electrodes are important devices for measuring the electrical activity that is always present in the brain and for acquiring EEG brainwave recordings. EEG recordings are useful for a broad range of applications including medical screening and diagnosis.

As a diagnostic aid, the rapid placement of EEG electrodes can be crucial in hospital and emergency room settings where medical or technical personnel use EEG recordings for diagnosing a variety of neurological disorders. In addition, the rapid and convenient placement of EEG electrodes for screening purposes in out-patient settings minimizes inconvenience to the patient.

Often, the most crucial EEG readings are obtained while unforeseen brain activity occurs. For example, EEG measurements taken during a seizure can help to determine the seizure focus region (i.e., the part of the brain in which the seizure activity begins). Other uses for EEG electrodes include measuring electrical brain activity during sleep. As such, an EEG electrode that is both comfortable and minimally disrupts the patient's sleep pattern is required for diagnosing sleep disorders. The availability of a rapid and conveniently deployed electrode is imperative for the development of portable consumer brain monitoring devices. A significant example would be an awareness device that monitors brain waves to prevent commercial drivers and others performing critical but repetitive operations from falling asleep.

Figure 1:
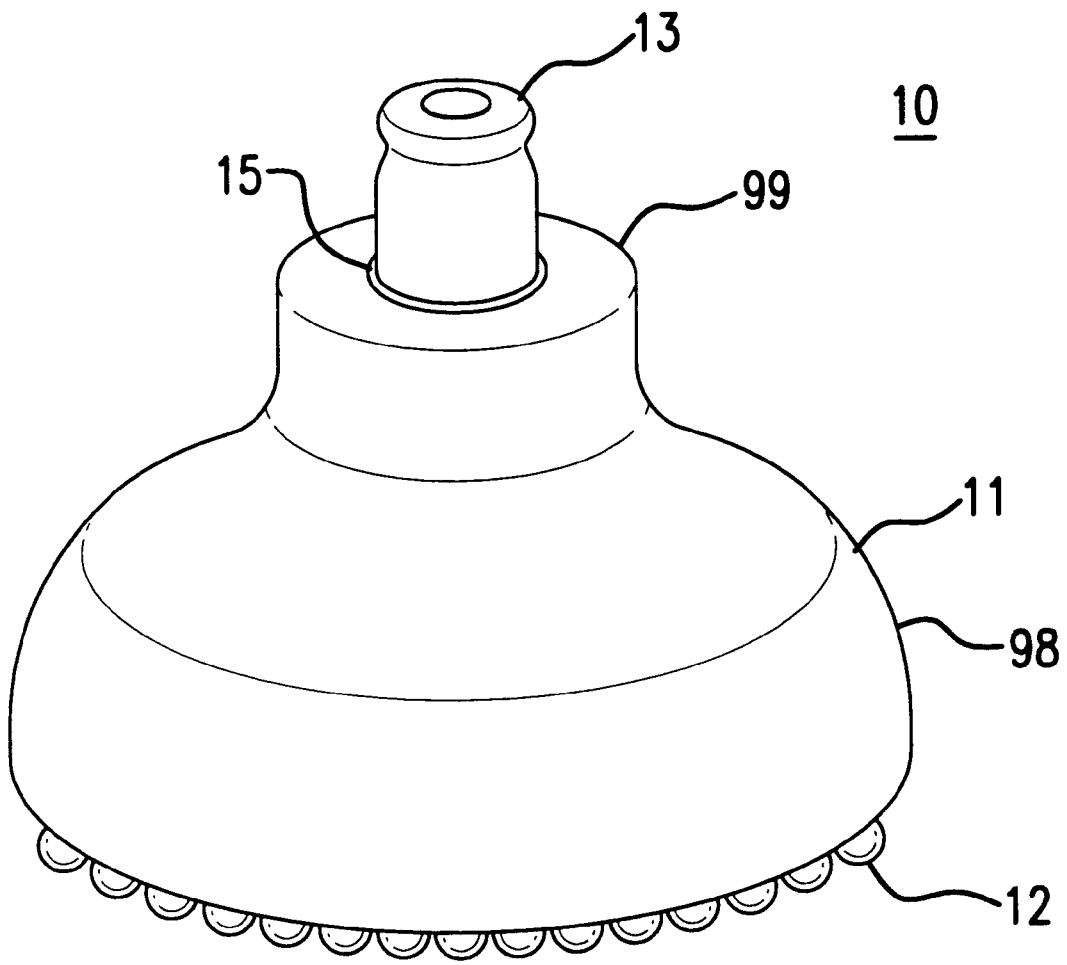
FIG. 1 is a perspective view of a quick-placement EEG electrode showing its general configuration.

FIG. 1 shows a quick-placement EEG electrode 10 for use in recording brain wave activity, for example. The EEG electrode includes a first element, housing, or fixed section, and one or more second elements or movable sections or parts, that connect to the first element and that operate in conjunction with the first element. In particular, the second elements are movable relative to the first element. In FIG. 1, the first element is shown as a cap 11, and the second elements are shown as a hair grabbing element 12 and a plunger 13. The cap 11 includes a hollow, hemispherical lower portion 98 and a hollow cylindrical upper portion 99. Other configurations for the first element are also possible, as will be described later. For example, the first element could be square or any polygon. The plunger 13 penetrates the upper portion 99 of the cap 11 through an opening 15. As shown in FIG. 1, the opening 15 is circular. However, the opening 15 may be any suitable shape, including that of any polygon. The plunger 13 can be placed in an engaged position or a disengaged position. In FIG. 1, the plunger 13 is shown disengaged. The positioning of the plunger 13 will be described later in more detail. Also as will be described later, the grabbing element 12 is attached to an underside of the lower portion 98 of the cap 11, and rests against a patient's scalp. The grabbing element 12 could include a tine set (not shown in FIG. 1) comprised of a number of flexible, S-shaped tines, hooks, or projections, arranged around a center section (not shown in FIG. 1). Alternatively, the grabbing element 12 could be a coil spring. In FIG. 1, the grabbing element 12 is shown in the open position.

In use, the grabbing element 12 is aligned with respect to the cap 11. A quick release mechanism (not shown in FIG. 1), including, for example, a guide and lock device, which will be described later, may be used to ensure proper alignment of the cap 11 and the grabbing element 12. Alternately, the alignment of the cap 11 and the grabbing element 12 may be obtained by a mechanism, which will be described later, for attaching the tine set to the cap 11.

Figure 2:
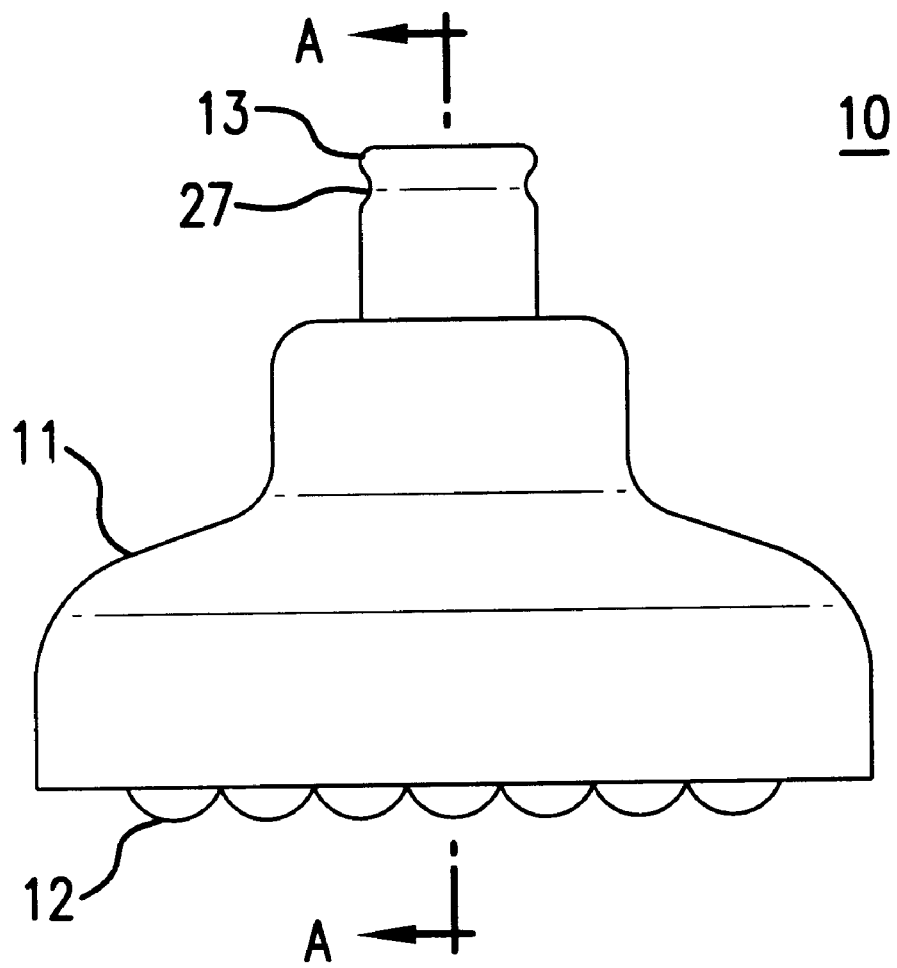
FIG. 2 is a side view of the quick-placement EEG electrode of FIG. 1.

FIG. 2 is a side view of the EEG electrode 10 showing the cap 11, the grabbing element 12, and the plunger 13 in the disengaged position. As shown in FIG. 2, the plunger includes a receptacle 27 that is used to attach the EEG electrode 10 to a recording device (not shown).

Figure 3:
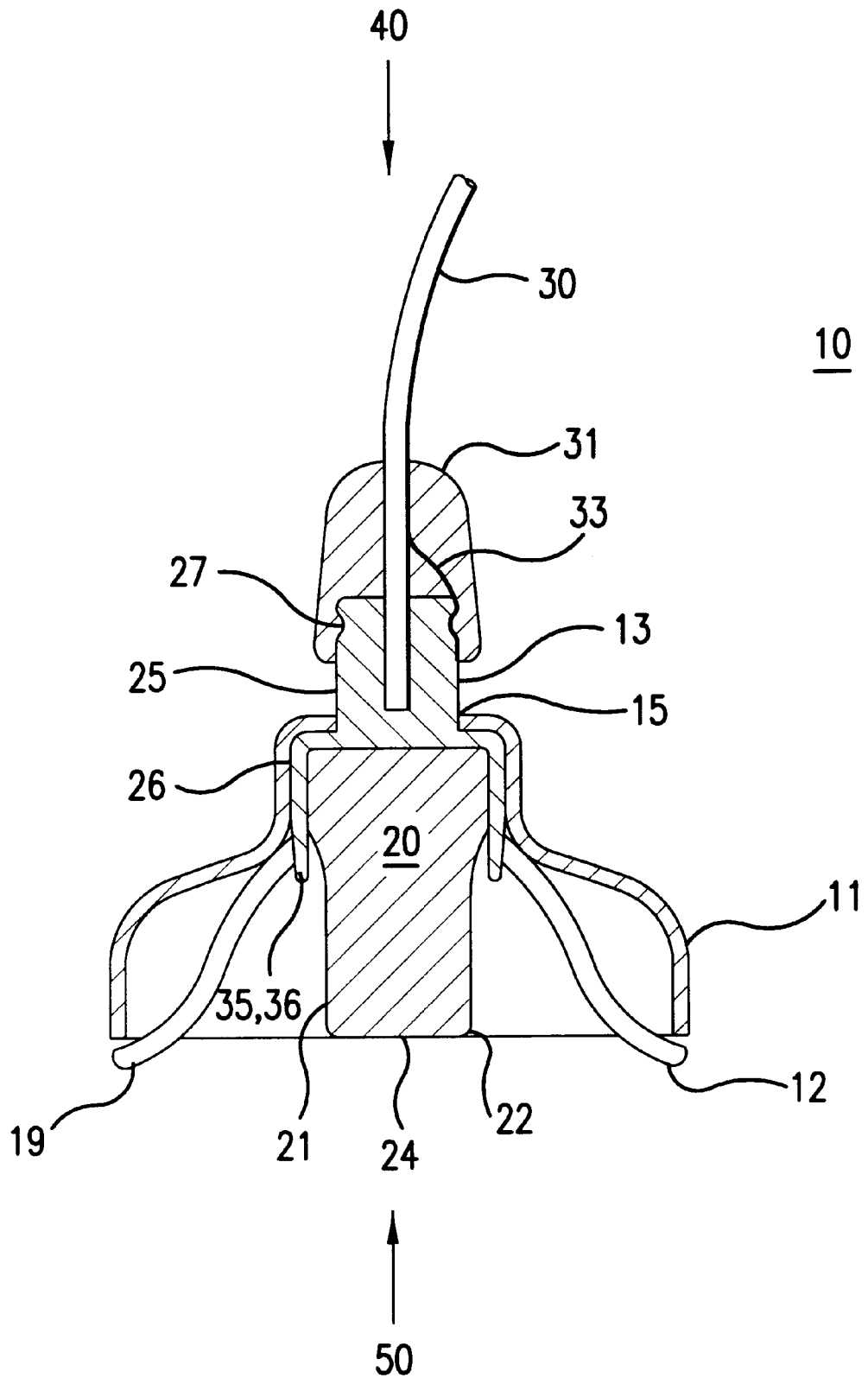
FIG. 3 is a cut-away view of the quick-placement EEG electrode as seen in the direction of the arrows A—A of FIG. 2.

FIG. 3 shows the EEG electrode 10 in cross-section in the direction of the arrows A—A of FIG. 2. Referring to FIG. 3, the plunger 13 includes an upper section 25 and a lower section 26. In FIG. 3, the upper section 25 and the lower section 26 are shown as cylindrical. However, the upper section 25 and the lower section 26 can be in the shape of any polygon to match a corresponding shape of the opening 15. The upper section 25 projects through the opening 15. The diameter of the lower section 26 may be larger than the diameter of the opening 15, thereby preventing the plunger 13 from exiting through the opening 15. A sponge 20, saturated with an electrolytic gel 21, and at least partly covered by a cover or a membrane 22, is encapsulated within the lower section 26 of the plunger 13. The sponge 20 may have a cross-section that corresponds to that of the lower section 26. For example, the sponge 20 may be cylindrical or in the shape of any polygon. Using the sponge 20 covered with the membrane 22 ensures that the electrolytic gel 21 will not evaporate during the time that the EEG electrode 10 is attached to the patient's scalp.

The sponge 20 may be attached to the EEG electrode 10 immediately prior to use, or may be attached when the EEG electrode 10 is manufactured, for example. Various methods may be used to attach the membrane 22, for example, by gluing or wrapping a thin membrane around the sponge 20 and then attaching the membrane 22 to an underside of the plunger 13. The membrane 22 may be attached to the underside of the plunger 13 by gluing, for example. The membrane 22 may be any suitable material such as a man-made polymeric material. The membrane 22 prevents the electrolytic gel 21 from leaking from the sponge 20 or evaporating while the EEG electrode 10 is not in use. A bottom 24 of the sponge defines an electrode contact point. The electrode contact point is part of a path for transmitting brain waves or similar information to the EEG electrode 10.

The EEG electrode 10 is connected to an EEG lead wire 30. Various known connection devices may be used for this purpose, such as a collar connector 31, which is placed over the plunger 13. The collar connector 31 is a "D" snap-in safety connector. Attached to the collar connector 31 is a leg wire 33. When pressed onto the top of the plunger 13, the collar connector 31 locks in place in the receptacle 27. The leg wire 33 on the collar connector 31 contacts a conductive layer, which will be described later, at the receptacle 27, completing an EEG circuit. This type of collar connector 31 and leg wire 33 are commercially available and commonly used with other EEG electrodes. Other commercially available connectors and leg wires may also be used with the EEG electrode 10.

The EEG electrode 10 shown in FIG. 3 may be of a small size with a diameter of the cap 11 being about one centimeter, for example. The cap 11 may be injection molded using acrylonitrile-butadiene-styrene (ABS) or similar material. The grabbing element 12 may be injected molded using Elastollan® thermoplastic polyurethane (TPU) or similar material or may be comprised of spring metal. The grabbing element 12 may be serrated or a coil spring. Other configurations may be used for a grabbing element. The plunger 13 may be injection molded and may be made of a material similar to that of the grabbing element 12. The plunger 13 may be coated with a conducting material that provides a current path between the electrolytic gel 21 and the leg wire 33. As shown in FIG. 3, the plunger 13 may be coated with a silver (Ag) layer 35, for example. Through an additional electrolytic process, a silver chloride (AgCl) layer 36 may be applied to the silver layer 35. The resulting Ag-AgCl layer conducts current from the electrolytic gel 21 to the leg wire 33. Other known coating and conductive layers may also be used with the plunger 13, or the plunger may be constructed from a conductive material such as carbon fiber filled plastic.

Once the EEG lead wire 30 is connected to the EEG electrode 10, the EEG electrode 10 is placed against hair at a point on the patient's scalp where recording is desired, with bottom portions 19 of the grabbing element 12 contacting the scalp. Some scalp hairs penetrate the openings in the grabbing element 12. The plunger 13 is then depressed to scoop and then trap the scalp hairs and hold the EEG electrode 10 in place. The grabbing element 12 securely holds the EEG electrode 10 in place against the scalp, and maximizes contact of the EEG electrode 10 with the scalp. The EEG electrode 10 is designed such that the trapped hairs exert a downward force, shown generally by arrow 40, to hold the EEG electrode 10 against the scalp.

The same downward force on the plunger 13 that traps the hairs in the grabbing element 12, also causes rapid compression of the sponge 20 in the center of the plunger 13. The compression of the sponge 20 ruptures the membrane 22, causing the electrolytic gel 21 to be applied to the scalp contact point. The membrane 22 is designed such that when the membrane 22 ruptures, ruptured sections of the membrane 22 are pulled away from the scalp contact area, thereby ensuring good electrical connection between the scalp contact point and the sponge 20. For example, lower cylindrical sides of the membrane 22 are not glued to the sponge 20. When the sponge 20 is compressed, the lower cylindrical sides of the membrane 22 retract upward along sides of the sponge 20, withdrawing the ruptured sections from the scalp contact point.

In addition to supplying the electrolytic gel 21, the compressed sponge 20 provides an upward force, shown generally by arrow 50, opposing a downward force being exerted by the hair trapped in the grabbing element 12, thereby creating an equilibrium system. The sponge 20, acting as a shock absorber, maintains constant contact with the scalp, even if the EEG electrode 10 moves up or down in relation to the scalp.

Figure 4:
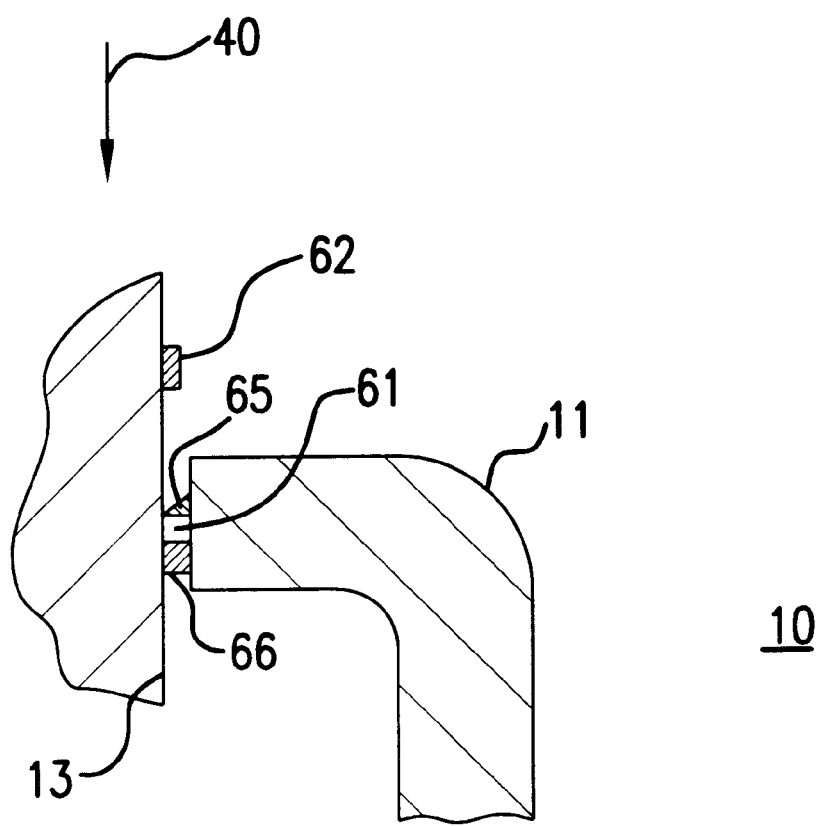
FIG. 4 is a cut-away view of the quick-placement EEG electrode of FIG. 1, revealing the details of a quick release mechanism.
Figure 5:
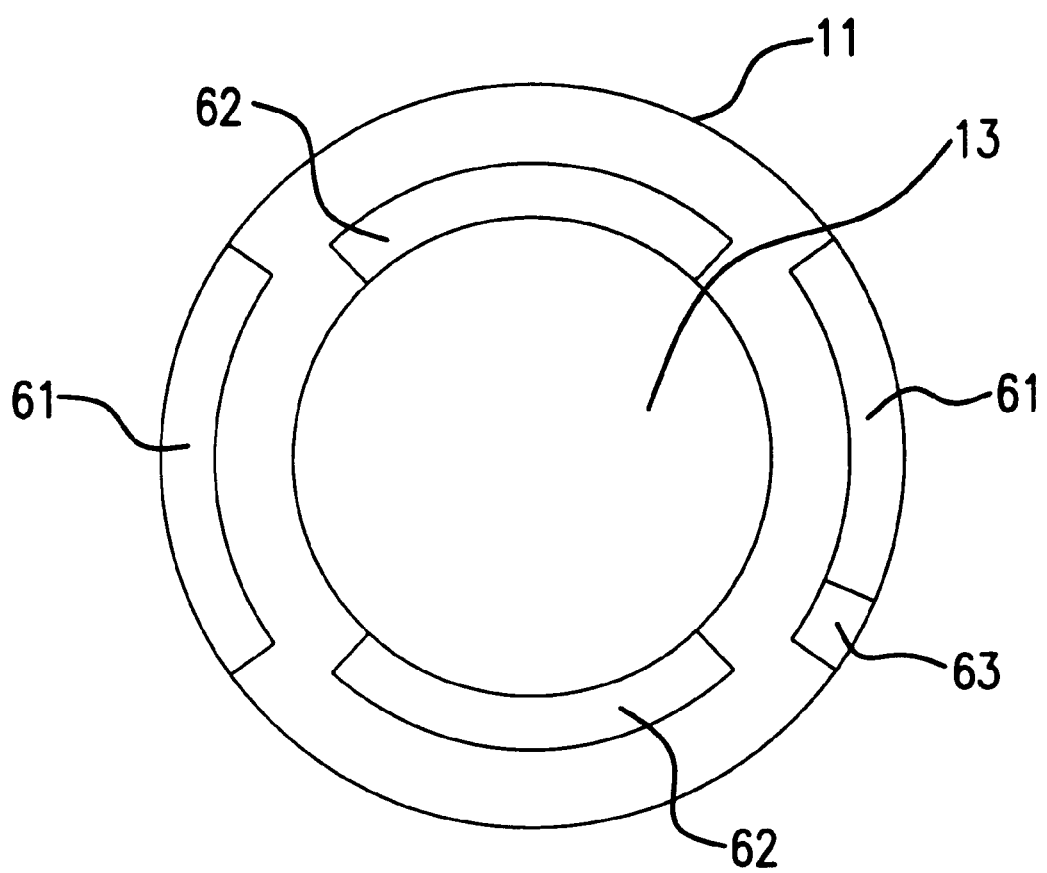
FIG. 5 is a top view of the quick release mechanism of FIG. 4.

FIGS. 4 and 5 show an example of a quick release mechanism that may be used with the EEG electrode 10. As shown in FIG. 5, two oppositely opposed locking grooves 61, each covering approximately 80 degrees of arc, partially encircle the interior wall of the cap 11. Corresponding break-away ridges 62 of about 80 degrees arc each partially encircle the plunger 13. As shown in FIG. 4, each locking groove 61 includes a curved upper ring 65 and a corresponding lower ring 66. Also as shown in FIG. 4, the upper rings 65 are curved in cross-section. Finally, a stop tab 63 (see FIG. 5) is located on the inner wall of the cap 11, above and at an end of one of the upper rings 65. To place the plunger 13 in the cap 11, the locking grooves 61 and the break-away ridges 62 are aligned such that the plunger 13 is insertable through the circular opening 15 in the cap 11. The plunger 13 is then rotated approximately 90 degrees so that the break-away ridges 62 lie above the locking grooves 61. Rotation beyond this point is prevented by the stop tab 63 that contacts an end of one of the break-away ridges 62.

In another embodiment, the quick release mechanism could include locking grooves and corresponding break-away ridges that are much shorter in arc than 80 degrees. In addition, only one, or more than two locking grooves and break-away ridges could be used. Other locking mechanisms such as detents and pins or springs could also provide for locking the plunger 13 in the engaged position.

To lock the EEG electrode 10 onto the scalp of a patient, using the locking mechanism shown in FIGS. 4 and 5, the downward force 40 is applied to the plunger 13. The downward force 40 on the plunger 13 causes a slight deformation of the upper portion of the cap 11. This deformation allows the break-away ridges 62 to slide over the curved upper rings 65 of the locking groves 61. The break-away ridges 62 then seat in the locking grooves 61, and lock the grabbing element 12 in the closed position.

To remove the EEG electrode 10 from the patient's scalp, the plunger 13 is again depressed. However, further depression is initially prevented by action of the lower rings 66 opposing the break-away ridges 62. Because the locking grooves 61 are square in cross section, downward forces generated from depressing the plunger 13 create stress in the break-away ridges 62 where the break-away ridges 62 attach to the plunger 13. When sufficient stress is applied to the break-away ridges 62, the break-away ridges 62 shear. The sheared break-away ridges 62 remain in the locking grooves 61. The compressive forces contained within the sponge 20 then cause the plunger 13 to rise up against the under side of the cap 11. The upward movement of the plunger 13 causes the projections of the grabbing element 12 to relax, allowing the EEG electrode 10 to be removed from the patient's scalp. The EEG electrode 10, removed in this manner, could be disposable.

The same quick release mechanism shown in FIGS. 4 and 5 may also be used without the break-away feature. In this example, the plunger 13 is locked in the cap 11 using the locking groves 61 and the break-away ridges 62 as before. To remove the EEG electrode 10, the plunger 13 is rotated so that the break-away ridges 62 are clear of the locking groves 61. The compressed sponge 20 then forces the plunger 13 upward, releasing the hairs trapped in the grabbing element 12. In this way, the EEG electrode 10 may be reused.

Figure 6:
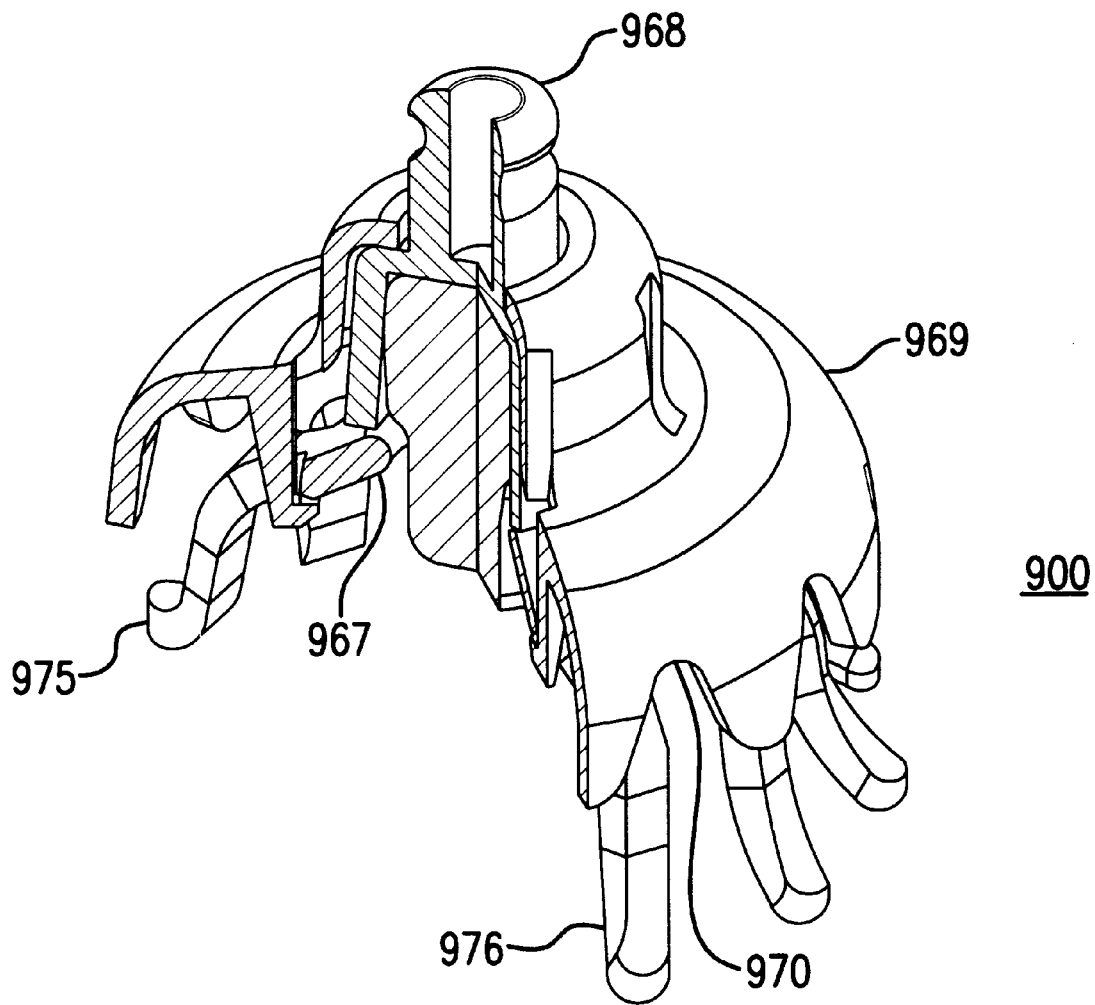
FIG. 6 is a cut-away perspective view of a quick-placement EEG electrode revealing the details of an additional quick release mechanism before deployment.
Figure 7:
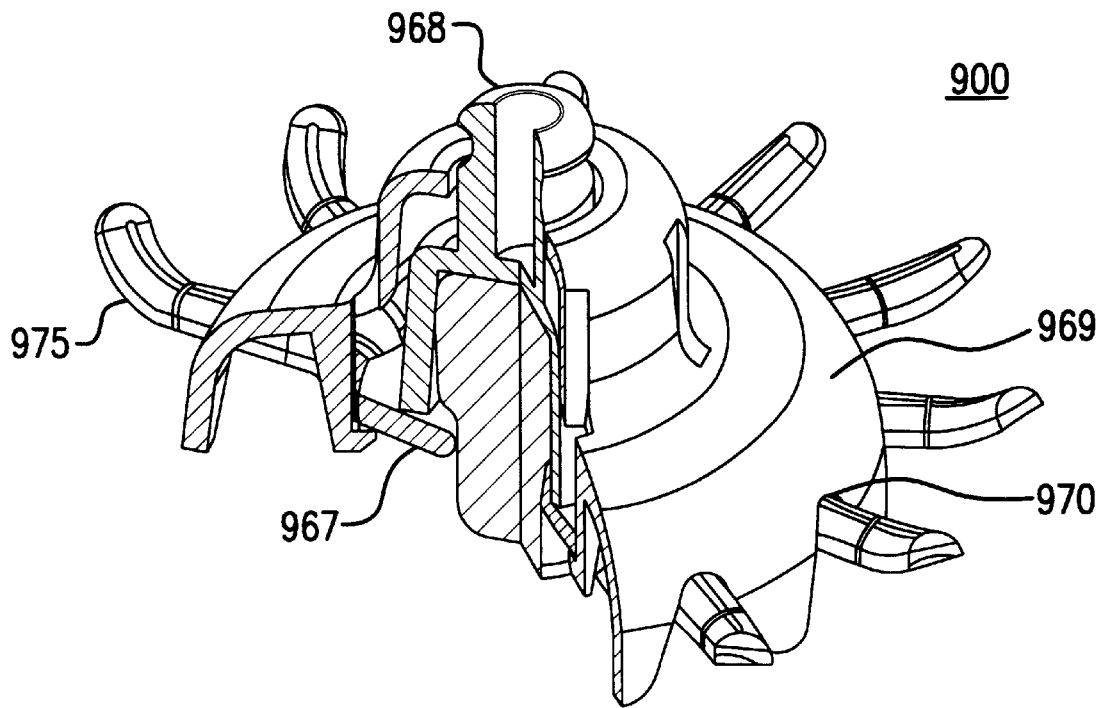
FIG. 7 is a cut-away perspective view of the quick-placement EEG electrode of FIG. 6 revealing the details of an additional quick release mechanism after deployment.

In an additional embodiment of an EEG electrode 900, the quick release mechanism could be implemented using a piece of flexible material that has two stable configurations as shown in FIGS. 6 and 7. In FIG. 6, a flexible ring 967 may be fabricated in a bowl shape with two stable configurations. The ring 967 is stable either as a concave ring or convex ring, and can be part of a tine set 975 that includes individual tines 976. Before the plunger 968 is depressed, the ring 967, in a convex state, orients the individual tines 976 pointing downward at an angle to the scalp. As the plunger 968 is depressed, pressure is placed on the top of the ring 967, causing the ring 967 to deform. The deformation causes the tines 976 to splay outwards and rake along the scalp. This action pushes and parts the hair away from a scalp contact point, ultimately maximizing contact with the scalp. Increasing pressure on the plunger 968 causes the ring 967 to further deform. Once the ring 967 has reached an elastomeric limit, the ring 967 will rapidly reverse orientation. Referring to FIG. 7, this will force the tines 976 into serrations 970 of the cap 969, trapping hair between the individual tines 976 and the serrations 970. To release the EEG electrode 900, the plunger 968 is pulled upward, causing the ring 967 to reverse orientation. This causes the tines 976 to assume a downward orientation, releasing the pressure against the cap 969, and releasing the EEG electrode 900 from the patient's scalp.

Figure 8:
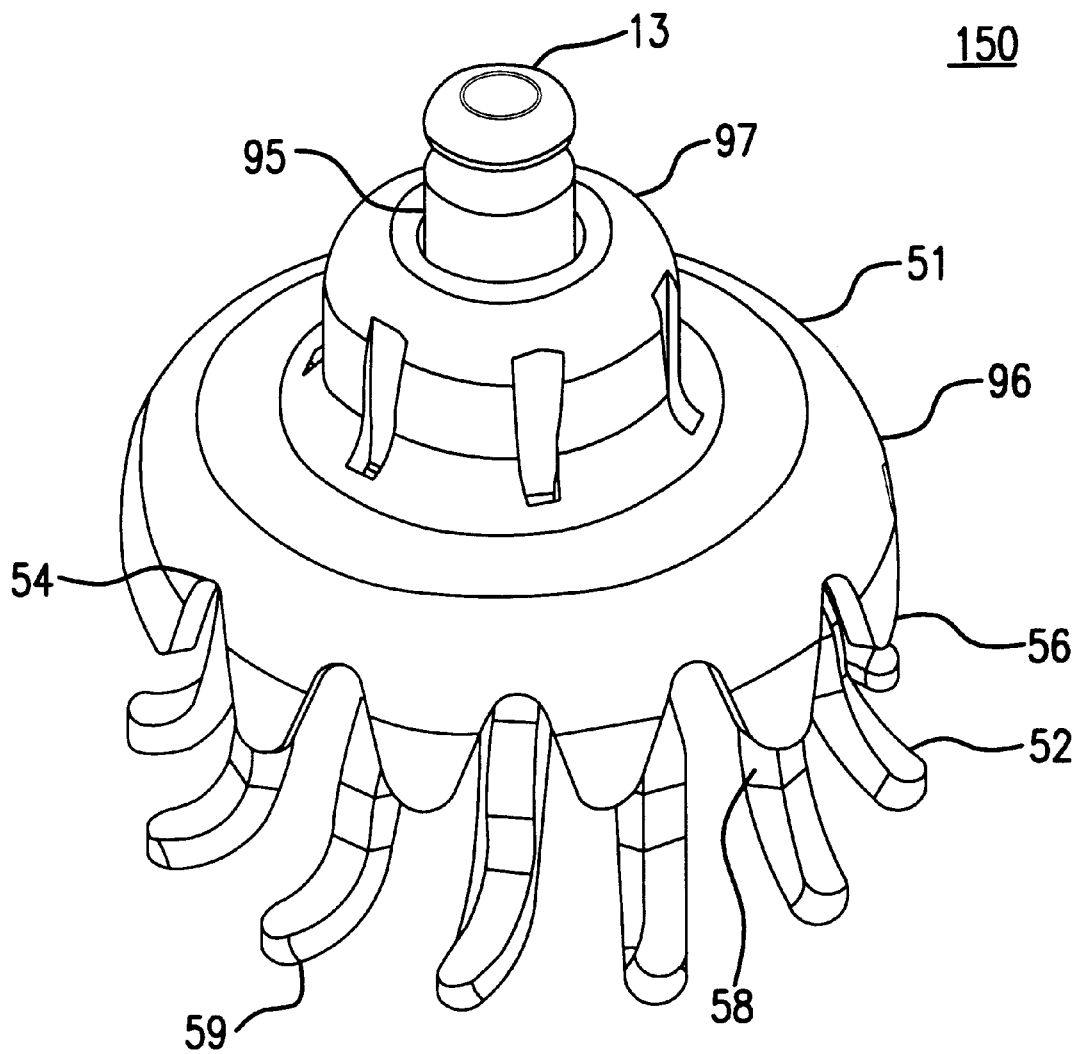
FIG. 8 is a perspective view of a quick-placement EEG electrode showing a tine set in the open position.

In an alternative embodiment, as shown in FIG. 8, an EEG electrode 150 includes a first element or fixed section, and one or more second elements or movable sections that connect to the first element and that operate in conjunction with the first element. In FIG. 8, the first element is shown as a cap 51, and the second elements are shown as a tine set 52 and a plunger 13. The cap 51 includes a hollow, hemispherical lower portion 96 and a hollow cylindrical upper portion 97. Other configurations for the first element are possible. For example, the first element could be any polygon. The plunger 13 penetrates the upper portion 97 of the cap 51 through an opening 95. As shown in FIG. 8, the opening 95 is circular. However, the opening 95 may be any suitable shape, including that of any polygon. The plunger 13 can be placed in an engaged position or a disengaged position. In FIG. 8, the plunger 13 is shown disengaged. The tine set 52 includes a number of flexible, S-shaped tines, or projections 58 arranged around a center section (not shown in FIG. 8). The projections 58 may be generally hemispherical in cross-section, with bottom portions 59 that rest against the scalp. The bottom portions 59 may be flat to allow the projections 58 to easily glide along the scalp when a downward force is applied to the tine set 52. The bottom portions 59 may also be padded or coated to ease application and comfort for the patient. In FIG. 8, the tine set 52 is shown in the open or not-flexed position.

The cap 51 includes a lower rim 56. As shown in FIG. 8, the rim 56 may include a number of serrations 54 along the circumference of the rim 56. As shown in FIG. 8, the serrations 54 are arcuate to accept the hemispherical projections 58. However, other configurations are possible for the serrations 54, including saw tooth and rectangular and square patterns. For saw tooth and square pattern serrations, the corresponding projections 58 would be saw tooth or square in cross-section, respectively.

In use, the tine set 52 is aligned with respect to the cap 51 so that the projections 58 fit between the serrations 54. A quick release mechanism, including, for example, a guide and lock device, as described above in conjunction with FIGS. 4 and 5, may be used to ensure proper alignment of the projections 58 and the serrations 54. Alternately, the alignment of the projections 58 and the serrations 54 may be obtained by the ring 967 described in conjunction with FIG. 6, or by a mechanism, which will be described later, for attaching the tine set 52 to the cap 51.

Figure 9:
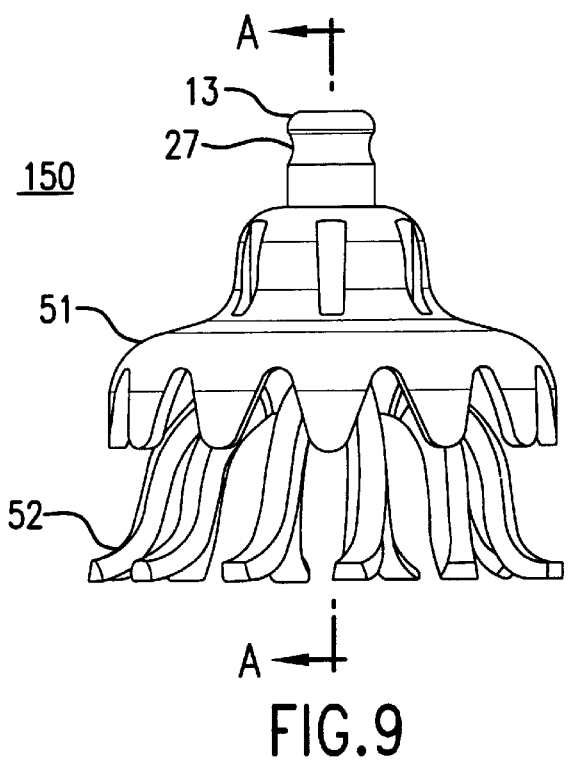
FIG. 9 is a side view of the quick-placement EEG electrode of FIG. 8 showing the tine set in the open position.

FIG. 9 is a side view of the EEG electrode 150 showing the cap 51, the tine set 52 having projections 58 in the open position, and the plunger 13 in the disengaged position. As shown in FIG. 9, the plunger 13 includes a receptacle 27 that is used to attach the EEG electrode 150 to a recording device (not shown).

Figure 10:
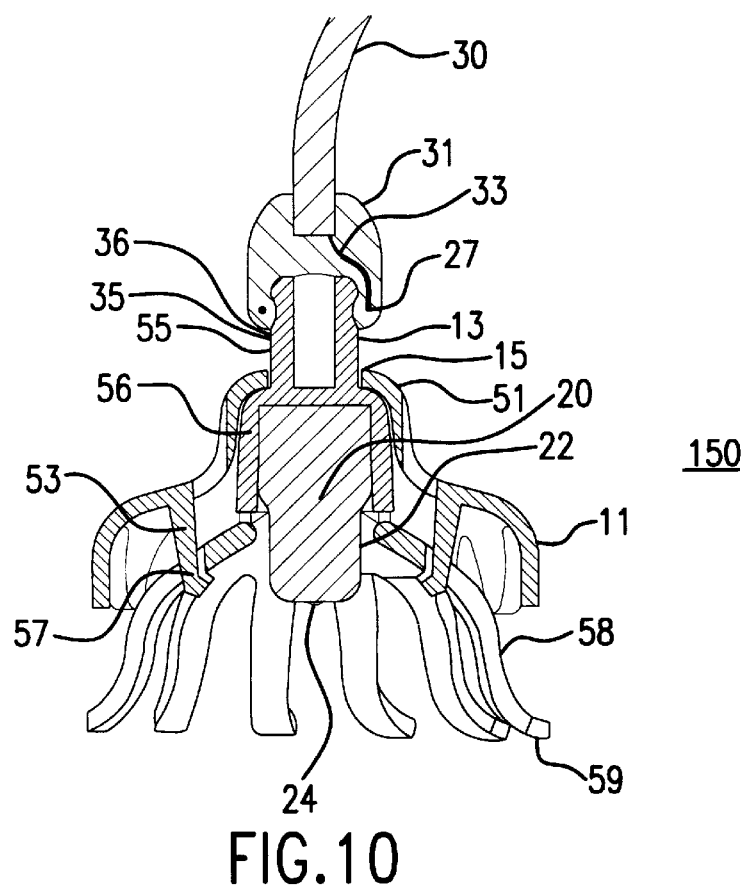
FIG. 10 is a cut-away view of the quick-placement EEG electrode of FIG. 8 as seen in the direction of the arrows A—A of FIG. 9.

FIG. 10 shows the EEG electrode 150 in cross-section in the direction of the arrows A—A of FIG. 9. Referring to FIG.

10, the plunger 13 includes an upper section 55 and a lower section 56. In FIG. 10, the upper section 55 and the lower section 56 are shown as cylindrical. However, the upper section 55 and the lower section 56 can be in the shape of any polygon to match the corresponding shape of the opening 95. The upper section 55 projects through the opening 95. A diameter of the lower section 56 may be larger than the diameter of the opening 95, thereby preventing the plunger 13 from exiting through the circular opening 95. A sponge 20 saturated with an electrolytic gel 21, and covered by a membrane 22, is encapsulated within the lower section of the plunger 13. The sponge 20 may have a cross sectional that corresponds to that of the lower section 56. For example, the sponge 20 may be cylindrical or in the shape of any polygon. Using the sponge 20 covered by a membrane 22 ensures that the gel 21 will not evaporate during the time that the EEG electrode 150 is attached to the patient's scalp.

The sponge 20 may be attached to the EEG electrode 150 immediately prior to use, or may be attached when the EEG electrode 150 is manufactured, for example. The operation and construction of the sponge 20 and the membrane 22 were previously described in conjunction with FIG. 3.

As shown in FIG. 10, the cap 51 may include downward projecting bayonet connectors 53 having L-shaped lower ends 57. The bayonet connectors 53 serve to lock the tine set 52 in place underneath a lower portion of the cap 51 and may be used to align the projections 58 with the serrations 54. The bayonet connectors 53 are sufficiently flexible so that when the center section of the tine set 52 is pressed against the bayonet connectors 53, the bayonet connectors 53 deflect, allowing the tine set 52 to move upward into the cap 51. The bayonet connectors 53 then snap back into place, securely locking the tine set 52 in place. Although the EEG electrode 50 could have one bayonet connector 53, preferably the cap 51 includes at least two connectors to ensure positive locking of the tine set 52 to the cap 51. Because the plunger 13 is located between the tine set 52 and the underside of the cap 51, the plunger 13 is prevented from falling out of the cap 51.

The EEG electrode 150 is connected to an EEG lead wire 30, for example, as previously described in conjunction with FIG. 3.

The EEG electrode 150 shown in FIG. 10 may be of a small size with a diameter of the cap 51 being about one centimeter, for example. The cap 51 may be injection molded using acrylonitrile-butadiene-styrene (ABS) or similar material. The tine set 52 may be injected molded using Elastollan® thermoplastic polyurethane (TPU) or similar material or comprised of spring steel. The tine set 52 may be serrated during the injection molding process to produce the projections 58. The plunger 13 may be injection molded and may be made of a material similar to that of the tine set and coated with an electrolytic material for example, as previously described in conjunction with FIG. 3.

Once the EEG lead wire 30 is connected, the EEG electrode 150 is placed against the hair on the patient's scalp where recording is desired, with the bottom portions 59 contacting the scalp. Some scalp hairs penetrate the openings formed between the projections 58 of the open tine set 52 and the serrations 54. The plunger 13 is then depressed to trap the scalp hairs and hold the EEG electrode 150 in place.

Figure 11:
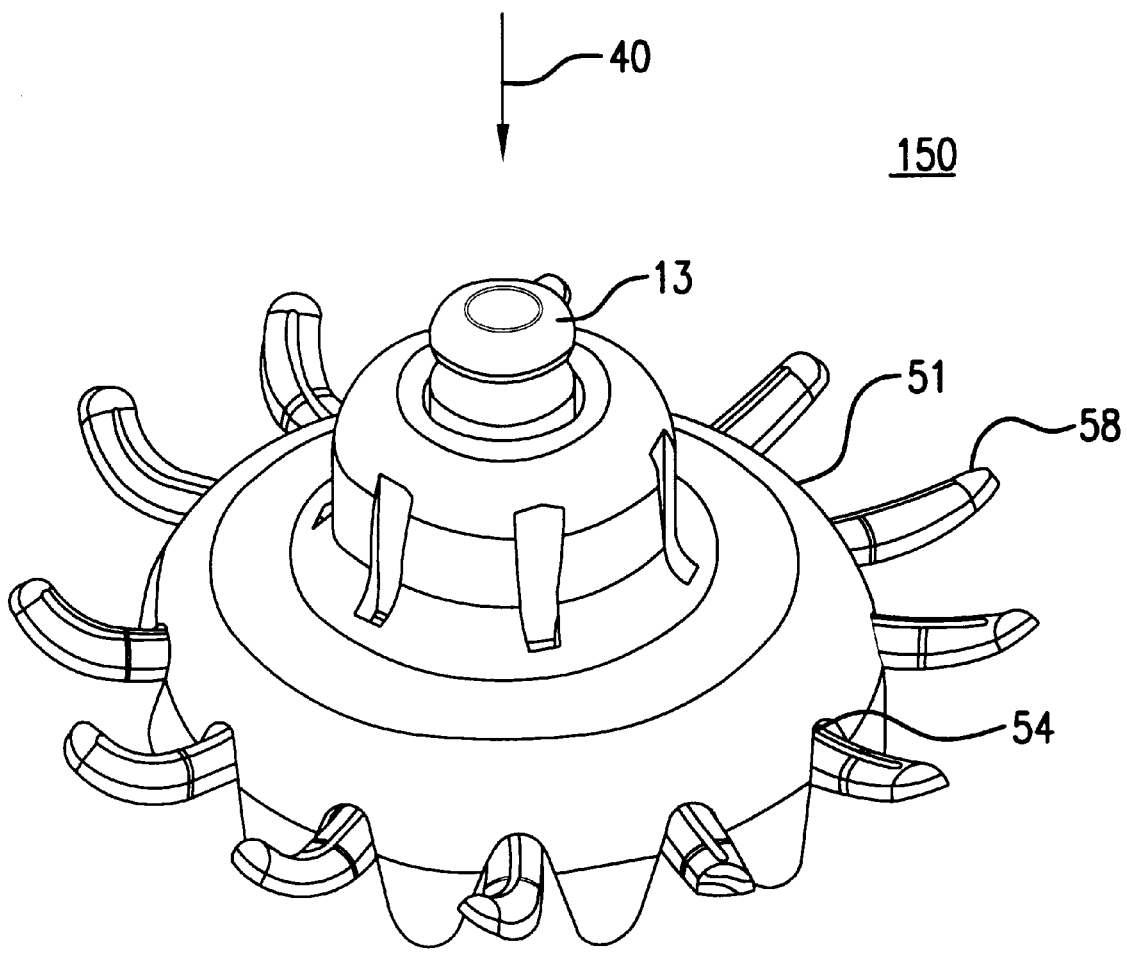
FIG. 11 is a perspective view of the quick-placement EEG electrode of FIG. 8 showing the tine set in the closed position.

FIG. 11 is a perspective view of the EEG electrode 150 after a downward force, shown generally by the arrow 40, has been exerted on the plunger 13. The downward force 40 causes the projections 58 to trap hairs in the serrations 54.

Figure 12:
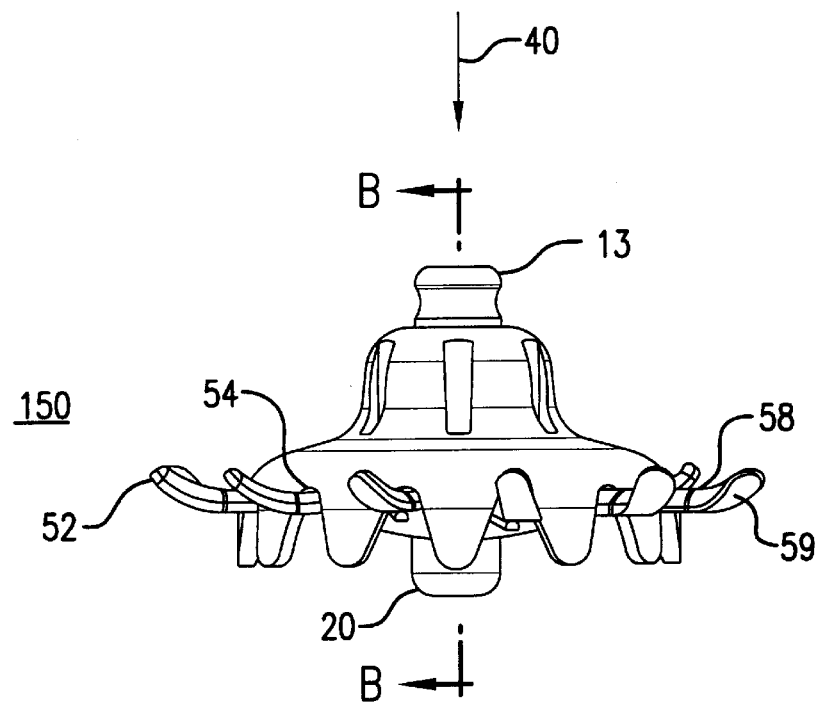
FIG. 12 is a side view of the quick-placement EEG electrode of FIG. 8 showing the tine set in the closed position.

FIG. 12 is a side view of the EEG electrode 150 showing the plunger 13 depressed and the projections 58 of the tine set 52 in the closed position, that is, splayed against the serrations 54. In operation, the downward force 40 applied to the top of the plunger 13 causes the tine set 52 to pivot about the L-shaped lower ends of the bayonet connectors 53. This pivoting motion causes the projections 58 to begin to splay. As pressure continues, the projections 58 slide out from the center of the EEG electrode 150 and the bottom portions 59 rake along the scalp. This action pushes and parts the hair away from the scalp contact point and maximizes the contact of the EEG electrode 150 with the scalp. As the splaying motion of the tine set 52 continues, the projections 58 rapidly reverse orientation, and the ends of the projections 58 are bent upward. When this happens, the hairs that have been raked by the bottom portions 59 are forced to slide up along the tops of the projections 58, and become wedged between the tops of the projections 58 and the serrations 54. The reoriented projections 58 are shown in FIG. 12 as being slightly curved upward. The EEG electrode 150 is designed such that when the projections 58 reach a limit of travel as defined by the serrations 54, hair is trapped in place between the projections 58 and the serrations 54. The trapped hairs exert a downward force to hold the EEG electrode 150 against the scalp.

Figure 13:
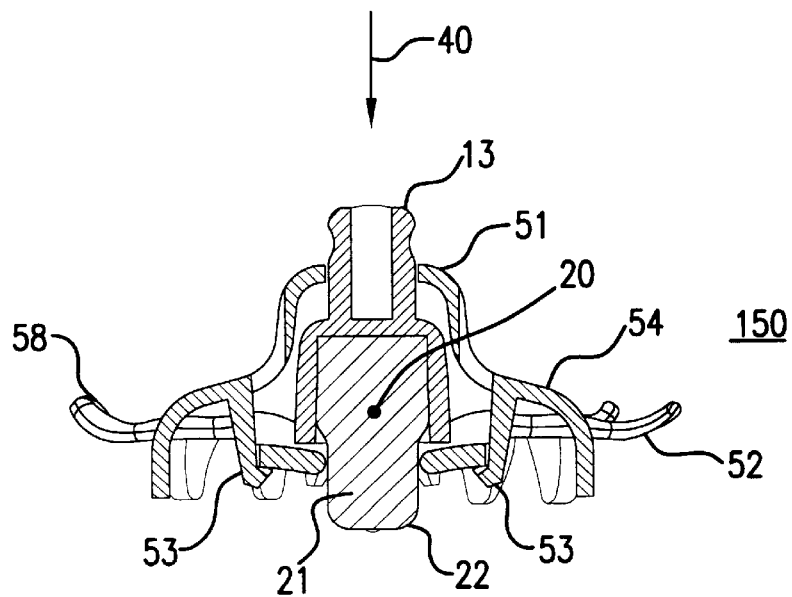
FIG. 13 is a cut-away view of the quick-placement EEG electrode of FIG. 8 as seen in the direction of the arrows B—B of FIG. 12.

FIG. 13 shows the EEG electrode 150 in cross-section in the direction of the arrows B—B of FIG. 12. The same downward force on the plunger 13 that traps the hairs between the serrations 54 and the tine set 52 during the orientation shift of the projections 58, also causes rapid compression of the sponge 20 in the center of the plunger 13, and whose operation is similar to that previously described in conjunction with FIG. 3.

In addition to supplying the electrolytic gel 21, the compressed sponge 20 provides an upward force, shown generally by arrow 50, opposing a downward force being exerted by the hair trapped between the projections 58 and the serrations 54, thereby creating an equilibrium system. The sponge 20, acting as a shock absorber, maintains constant contact with the scalp, even if the EEG electrode 50 moves minutely up or down in relation to the scalp.

As previously described in conjunction with FIGS. 4 and 5, the EEG electrode 150 may employ a quick release mechanism for removing the EEG electrode 150 from the patient's scalp.

In another embodiment, the cap 51 may have a rim 56 without serrations 54. In this embodiment, the hairs from the patient's scalp are trapped between the projections 58 and the rim 56.

Figure 14:
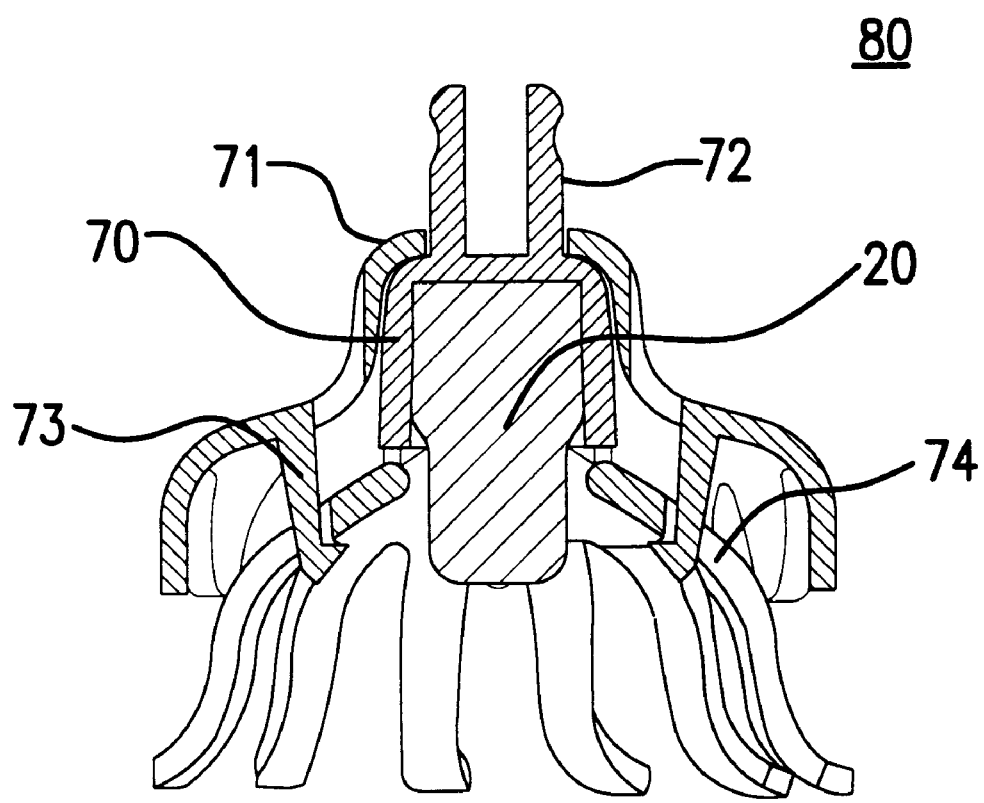
FIG. 14 shows another embodiment of the EEG electrode.

FIG. 14 shows another embodiment of a quick release EEG electrode. In, the embodiments described above, the tine set 52 and the plunger 13 are separate pieces in communication with each other when assembled. FIG. 14 shows a single movable element 70 that may be combined with the cap 51 and the sponge 20 of prior embodiments to produce a quick placement EEG electrode 80. The movable element includes a plunger section 72 formed continuously with a tine section 74. The movable element 70 incorporates all the necessary features of the separate tine set and the plunger shown, for example, in FIG. 10. The movable element connects to the cap using the bayonet connectors 73.

Figure 15:
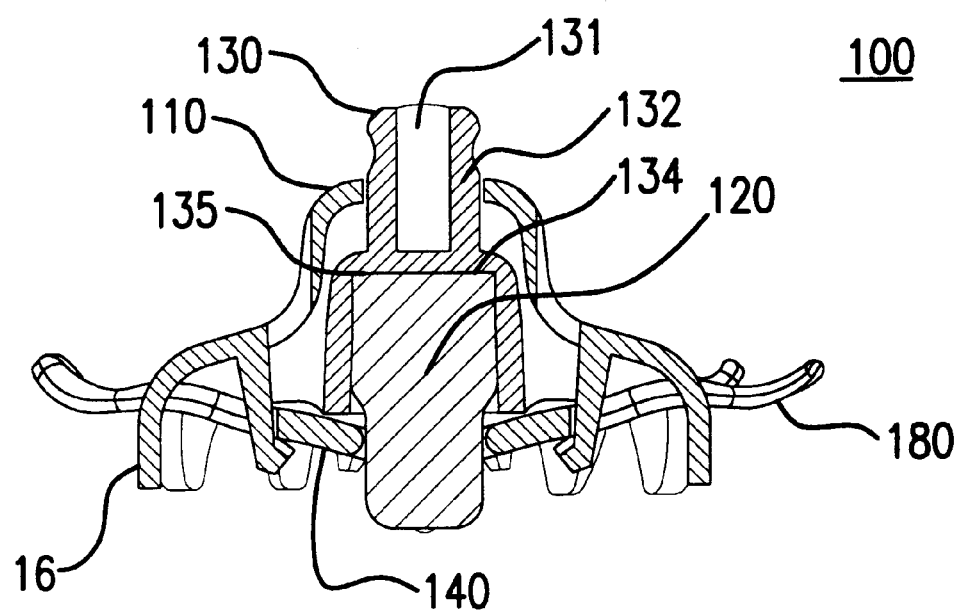
FIG. 15 shows another embodiment of the EEG electrode.

FIG. 15 shows another embodiment of a quick release EEG electrode 100. The construction of the EEG electrode 100 is similar in most respects to the EEG electrode 900 shown in FIG. 8. However, in FIG. 15, the EEG electrode 100 may be assembled and placed on the patient's scalp without a sponge 120. After the EEG electrode is in place, the sponge 120, which is loaded with electrolytic gel 21, may then be inserted to complete assembly of the EEG electrode 100.

In FIG. 15, the EEG electrode 100 includes a cap 110, a grabbing element 180, a plunger 130 and the sponge 120. The plunger 130 is similar to the plunger 13 shown in FIG. 10, except that the plunger 130 includes a central cavity 131 that extends from an upper section 132 through a lower section 134 of the plunger 130. The lower section 134 includes a shoulder 135. The plunger 130 acts as before to activate the grabbing element 180 to trap hair.

Figure 16:
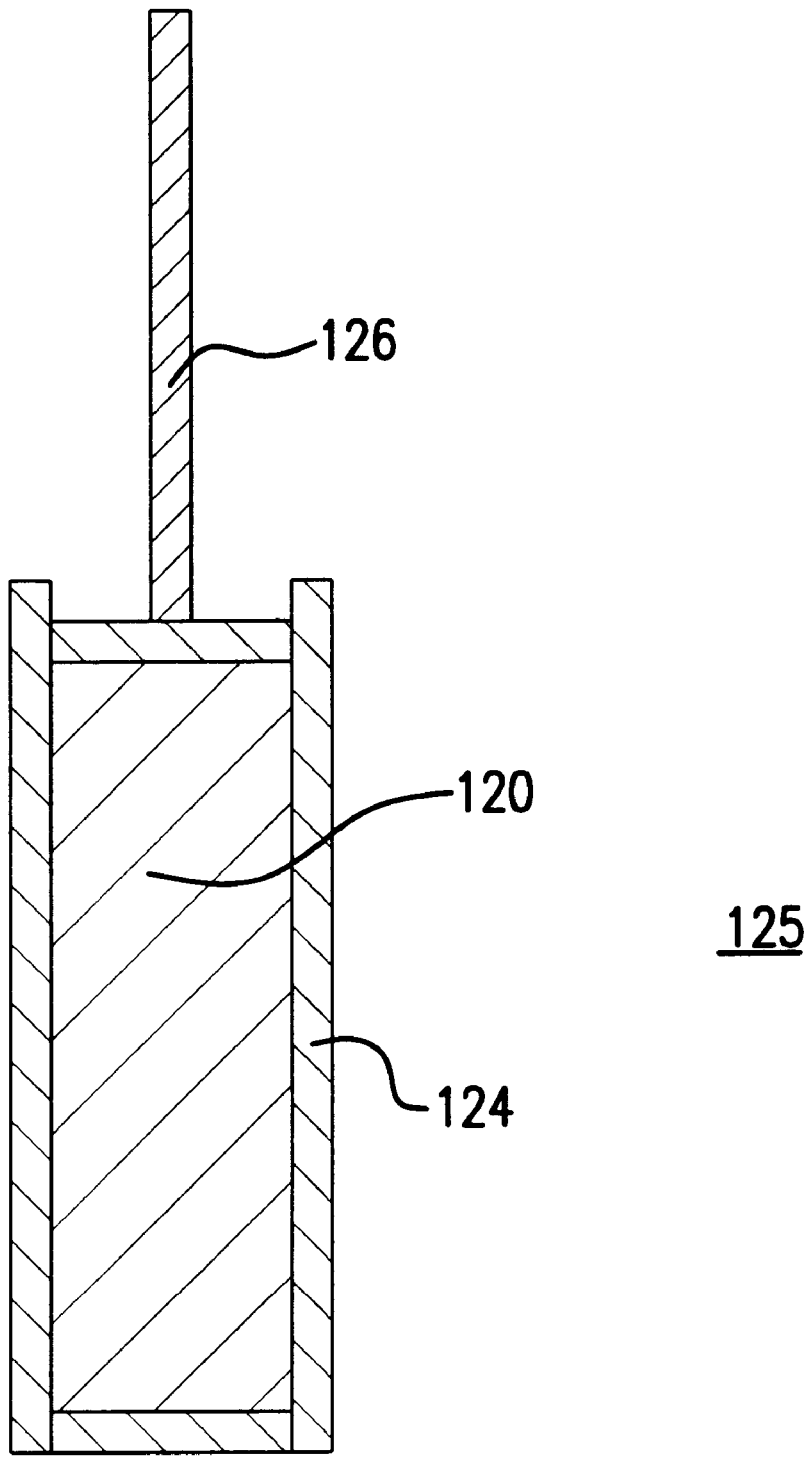
FIG. 16 shows a sponge dispenser for use with the EEG electrode.

Once the electrode is placed on the patient's scalp, the sponge 120 may be loaded through the central cavity 131. The sponge 120 may be loaded by using a sponge dispenser 125 as shown in FIG. 16. The sponge dispenser 125 may include a tube 124. The tube 124 may be a hollow cardboard or plastic tube, for example. The sponge 120, saturated with the electrolytic gel 21, is stored in the dispenser 125. Alternatively, the gel 21 may be added to the sponge 120 just prior to inserting the sponge 120 into the electrode 100. The sponge 120, while stored in the dispenser 125, is radially compressed. An inside diameter of the dispenser 125 matches a diameter of the central cavity 131. Finally, the dispenser includes a plunger 126 to push the sponge 120 out of the tube 124.

To insert the sponge 120 into the central cavity, the dispenser 125 is placed above the plunger 130, and the sponge 120 is ejected by pushing down on the sponge 120 using the plunger 124. When the sponge 120 reaches the lower sections 134, it expands to fill the larger diameter opening available. The sponge 120 is then held in place by the frictional fit within the lower section 134 and by the shoulder 135. The sponge 120 may be inserted into the EEG electrode 100 either before or after attachment of the electrode to the patient's scalp.

Figure 17:
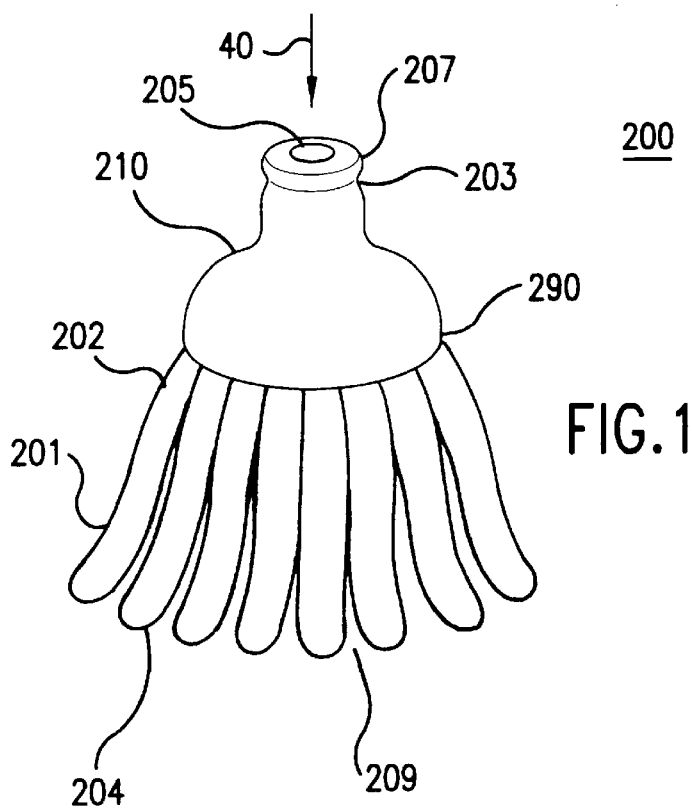
FIG. 17 shows another embodiment of the EEG electrode.

Another embodiment of the EEG electrode is shown in FIG. 17. An EEG electrode 200 includes a first element or fixed section, and a second element or movable section connected to the first element. The second element operates in conjunction with the first element. In FIG. 17, the first element is shown as a cap 210, and the movable element is shown as a tine set 202. The cap 210 includes a hollow cylindrical upper portion 207. Other configurations for the fixed element are also possible. As shown in FIG. 17, the cap 210 includes a circular opening 205. However, the opening 205 in may be any suitable shape, including that of a polygon. The tine set 202 is attached to the underside of the lower portion 290 of the cap 210. The tine set 202 includes a number of flexible tines or projections 201, arranged around the circumference of the cap 210. The projections 201 may be hemispherical in cross-section, with bottom portions 204 that rest against the scalp of a patient. A gap 209 exists between adjacent projections 201 when the tine set 202 is in a relaxed condition as shown in FIG. 17. The bottom portions 204 may be flat to allow the projections 201 to easily glide along the scalp when a downward force 40 is applied to the EEG electrode 200.

Attached to the underside of the cap 210 in the hollow cylindrical upper portion 207, is a membrane-encapsulated sponge (not shown in FIG. 17). The sponge may be attached to the EEG electrode 200 immediately prior to use, or may be attached when the EEG electrode 200 is manufactured, for example, as previously described in conjunction with FIG. 3.

The EEG electrode 200 in FIG. 17 is connected to an EEG lead (not shown). Various known connection devices may be used for this purpose, such as the collar connector (not shown), as previously described in conjunction with FIG. 3.

The EEG electrode 200 shown in FIG. 17 may be of small size with a cap diameter of about one centimeter, for example. The cap 210 may be injection molded using acrylonitrile-butadiene-styrene butadiene-styrene (ABS) or similar material. The tine set 202 may be injection molded using Elastollan® thermoplastic polyurethane (TPU) or similar material or spring steel. The tine set 202 may be serrated during the injection molding process to produce the projections 201. Alternatively, the cap 210 and tine set 202 could be molded as one piece. The tine set 202 and cap 210 may be coated with or entirely consist of a conducting material, for example, as previously described in conjunction with FIG. 3.

Figure 18:
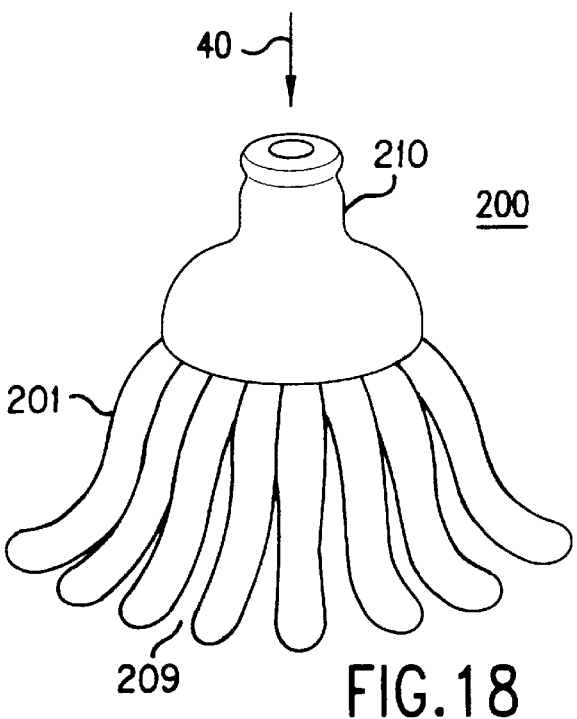
FIG. 18 shows the EEG electrode of FIG. 17 being depressed.
Figure 19:
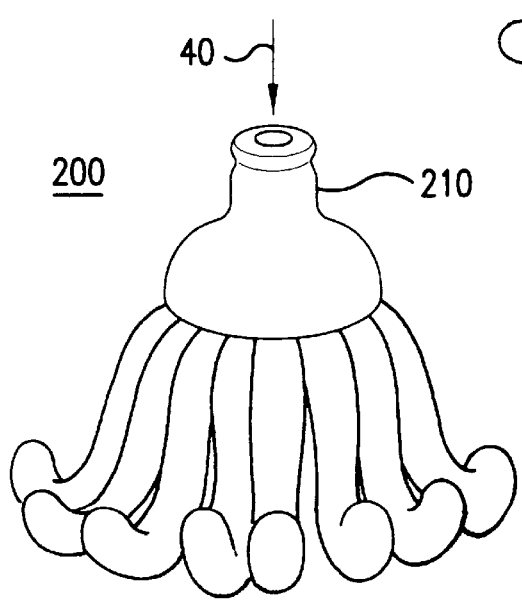
FIG. 19 shows the EEG electrode of FIG. 17 in a trapped position.

Once the EEG electrode 200 is placed on the scalp where recording is desired, bottom portions 204 of the projections 201 contact the scalp. Referring to FIG. 18, after a downward force, shown generally by the arrow 40, has been exerted on the EEG electrode 200, the projections 201 move radially outward and channel hair into the gaps 209 between the projections 202. Continued downward pressure 40 causes the projections 202 to splay and reverse orientation as shown in FIG. 19. When the projections 201 reverse orientation, the projections 201 move upward while simultaneously closing the gaps 209 between the projections 201. This action pinches the hairs and exerts an upward force 50, thereby firmly anchoring the EEG electrode 200 against the scalp.

The same downward force on the cap 210 that traps the hairs in the projections 201, also causes rapid compression of the sponge attached inside the cap 210. Operation of the sponge is the same as that described in conjunction with FIG. 3.

To remove the EEG electrode 200 from the scalp, the cap 210 is again depressed. Continued downward pressure will break the projections 201 from the cap 210 and release the EEG electrode 200 from the hair.

Figure 20:
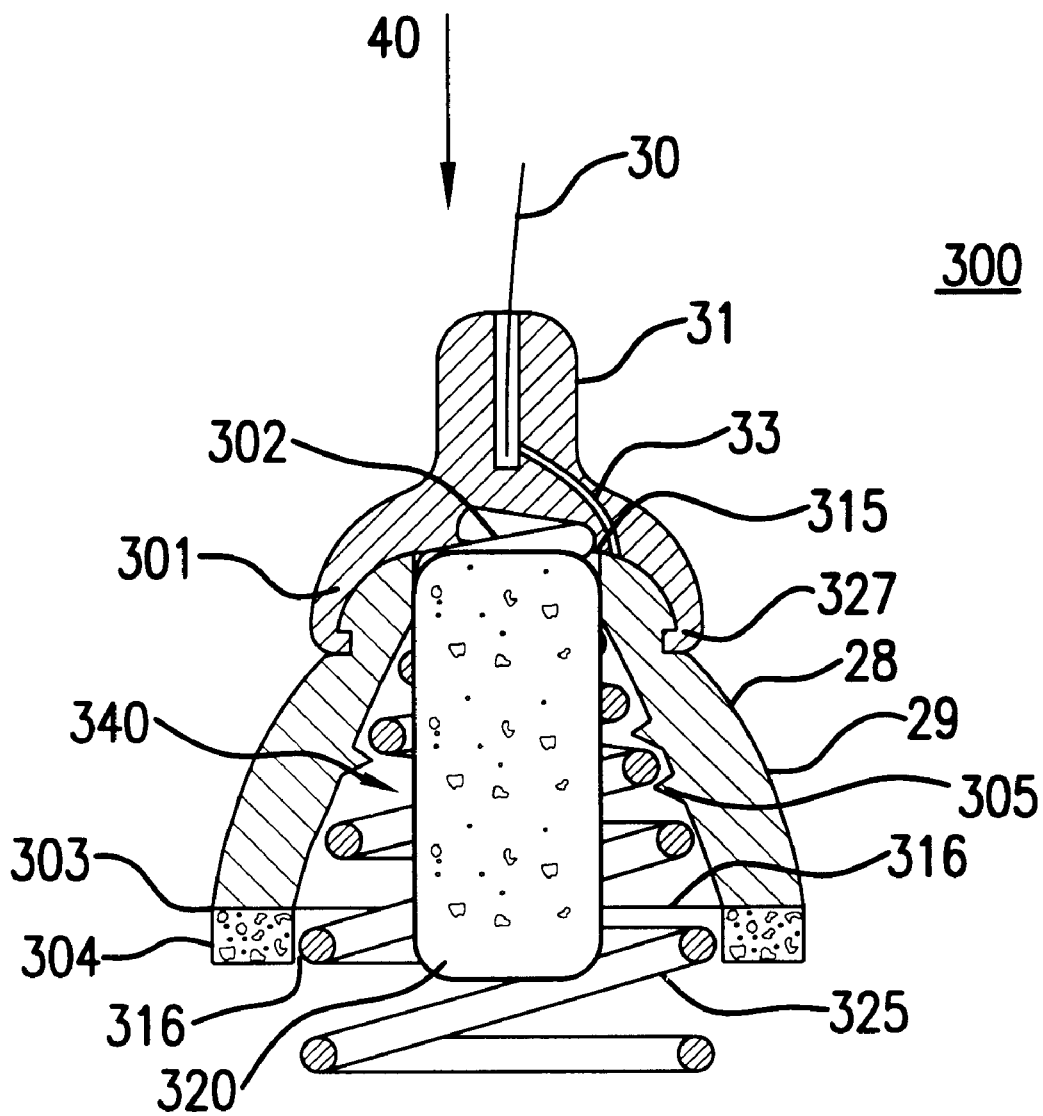
FIG. 20 is a cut-away view of another embodiment of the EEG electrode.

In another embodiment, as shown in FIG. 20, an EEG electrode 300 includes a first element or fixed section, and one or more second elements or movable sections that connect to the fixed section and that operate in conjunction with the fixed section. In FIG. 20, the fixed section is shown as a cap 301, and the movable section is shown as a conical, coil spring 302 having winds 340. The winds 340 may be open or closed. The cap 301 may be a hollow, hemispherical shape, and may incorporate a top circular opening 315 and a bottom circular opening 316. A diameter of the top opening 315 is smaller than a diameter of the bottom opening 316. Other configurations for the fixed section are possible. For example, the fixed section could be any polygon, the top opening 315 and bottom opening 316 could be the same diameter, and the spring 302 could be a cylindrical shape.

The cap 301 includes a lower rim 303. As shown in FIG. 20, the rim 303 may include a sponge 304 attached to a circumference of the rim 303. The cap 301 also includes a receptacle 327 that is used to attach the EEG electrode 300 to a recording device (not shown). A sponge 320 saturated with an electrolytic gel 21, and covered by a membrane 322, may be encapsulated within the coil spring 302. The sponge 320 may have a cross section that corresponds to that of the coil spring 302. For example, the sponge 320 may be cylindrical or in the shape of any polygon. Using the sponge 320 saturated with electrolytic gel 21 ensures that the electrolytic gel 21 will not evaporate during the time that the EEG electrode 300 is attached to the patient's scalp.

The sponge 320 may be attached to the EEG electrode 300 immediately prior to use, or may be attached when the EEG electrode 300 is manufactured, for example, as previously described in conjunction with FIG. 3.

As shown in FIG. 20, the cap 301 may include projecting ridges 305 which serve to lock the spring 302 in place underneath the cap 301. The ridges 305 are sufficiently flexible so that when the cap 301 is pressed against the spring 302, the ridges 305 deflect, allowing the spring 302 to move upward into the cap 301. The ridges 305 then snap back into place, securely locking the spring 302 in place within the cap 301. Although the EEG electrode 300 could have one ridge 305, preferably the cap 301 includes at least two ridges 305 to ensure positive locking of the spring 302 to the cap 301.

The EEG electrode 300 is connected to an EEG lead 30 as previously described in conjunction with FIG. 3.

The EEG electrode shown in FIG. 20 may be of small size with a diameter of the cap 301 being about 2 centimeters, for example. The cap 301 may be injection molded using acrylonitrile-butadiene-styrene (ABS) or similar material. The spring 302 may be Elastollan® thermoplastic polyurethane (TPU) or similar material, or comprised of spring steel. The cap 301 is coated with a conducting material as previously disclosed in conjunction with FIG. 3.

Once the EEG lead 30 is connected, the EEG electrode 300 is placed at a point on the patient's scalp where recording is desired, with a bottom portion 325 of the spring 302 contacting the scalp. Some scalp hairs penetrate the open winds 340 of the spring 302. The EEG electrode 300 is then rotated by hand, for example, to draw hair into the winds 340 of the spring 302. After the spring 302 is rotated until it is snug against the scalp, downward pressure, shown generally by the arrow 40, is applied to the cap 301 and the cap 301 is pressed over the spring 302. The ridges 305 inside the cap 301 engage the spring 302, compressing the open winds 340, and thereby trapping hair between the spring 302 and cap 301. The downward pressure 40 also compresses the sponge 304 on the bottom of the cap's lower rim 303. The trapped hairs exert a downward force to hold the EEG electrode 300 against the scalp.

The same downward force on the spring 302 that traps the hairs between closed winds 340 of the spring 302 also causes compression of the sponge 320 in the center of the spring 302. The operation of the sponge 320 is the same a previously described in conjunction with FIG. 3.

The compressed sponge 320 provides an upward force, opposing the downward force being exerted by the hair trapped between the closed winds 340 of the spring 302 and the cap 301, thereby creating an equilibrium system. The sponge 320, acting as a shock absorber, maintains constant contact with the scalp, even if the EEG electrode 300 moves up or down in relation to the scalp.

The EEG electrode 300 may be removed by rotating the cap 301 and spring 302 in a direction opposite of that for emplacement.

Figures 21, 22:
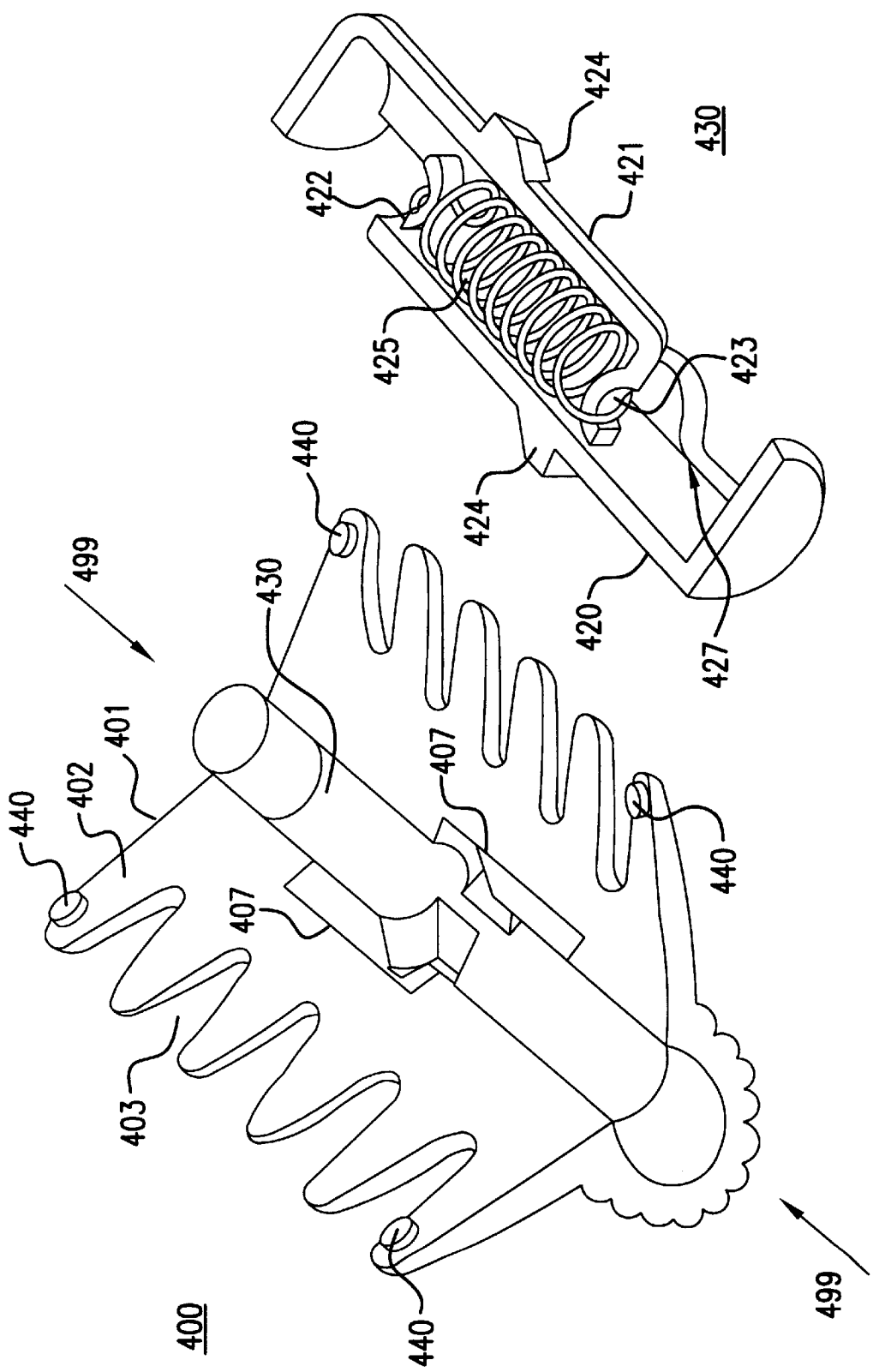
FIG. 21 is a perspective view of an EEG electrode.
FIG. 22 is a cut-away view of the extender unit of the EEG electrode of FIG. 21.
Figure 23:
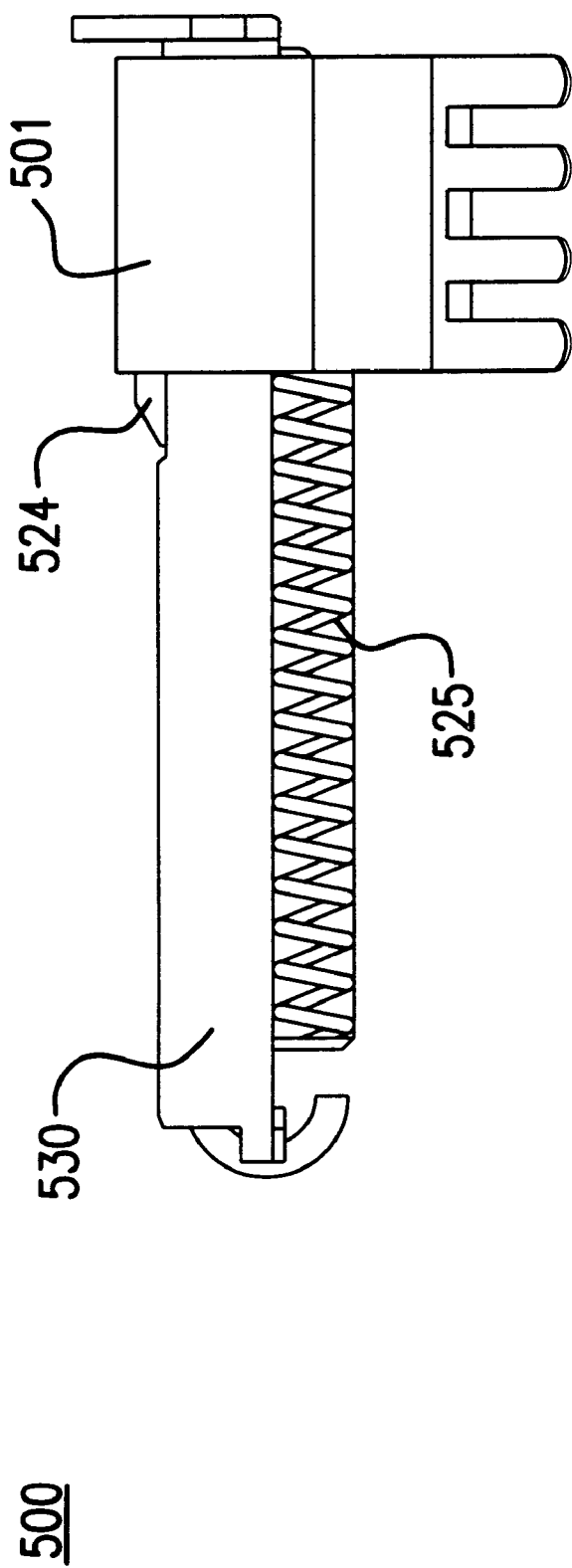
FIG. 23 is a side view of another embodiment of the EEG electrode, before placement on the scalp.
Figure 24:
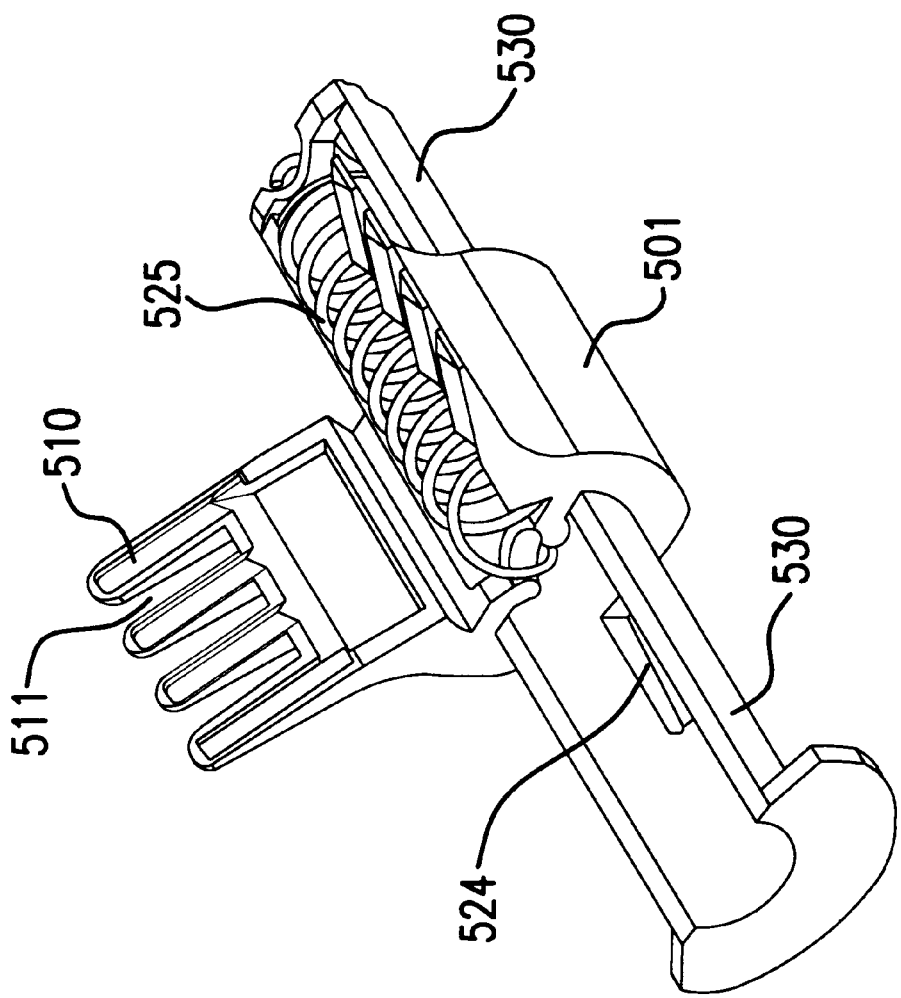
FIG. 24 is a perspective view of the EEG electrode of FIG. 23, after placement on the scalp.
Figure 25:
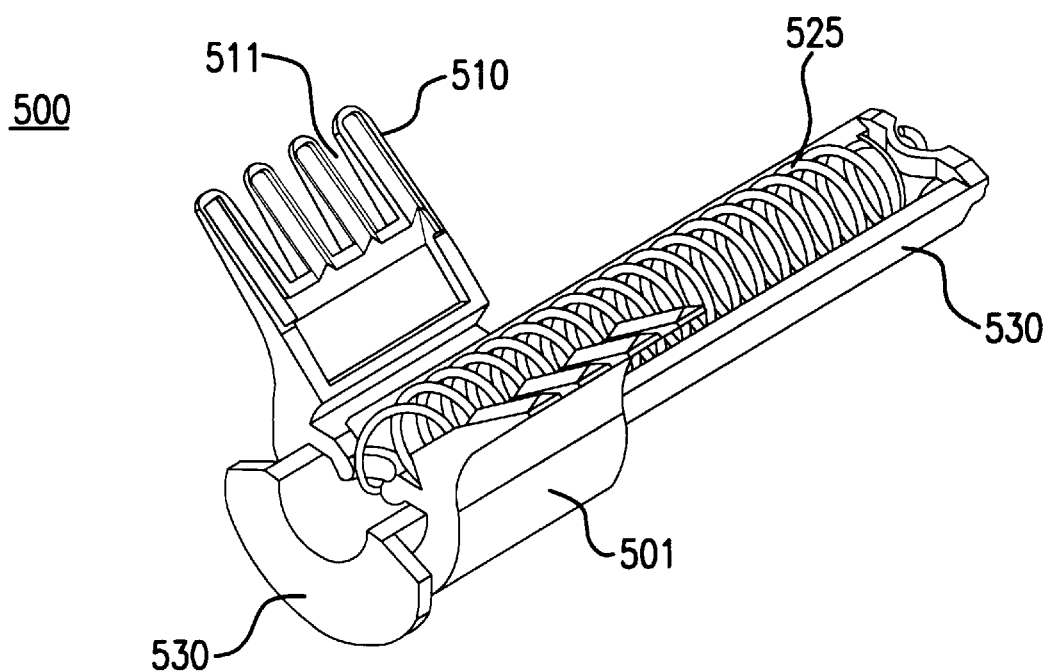
FIG. 25 is a perspective view of the EEG electrode of FIG. 23, before placement on the scalp.
Figure 26:
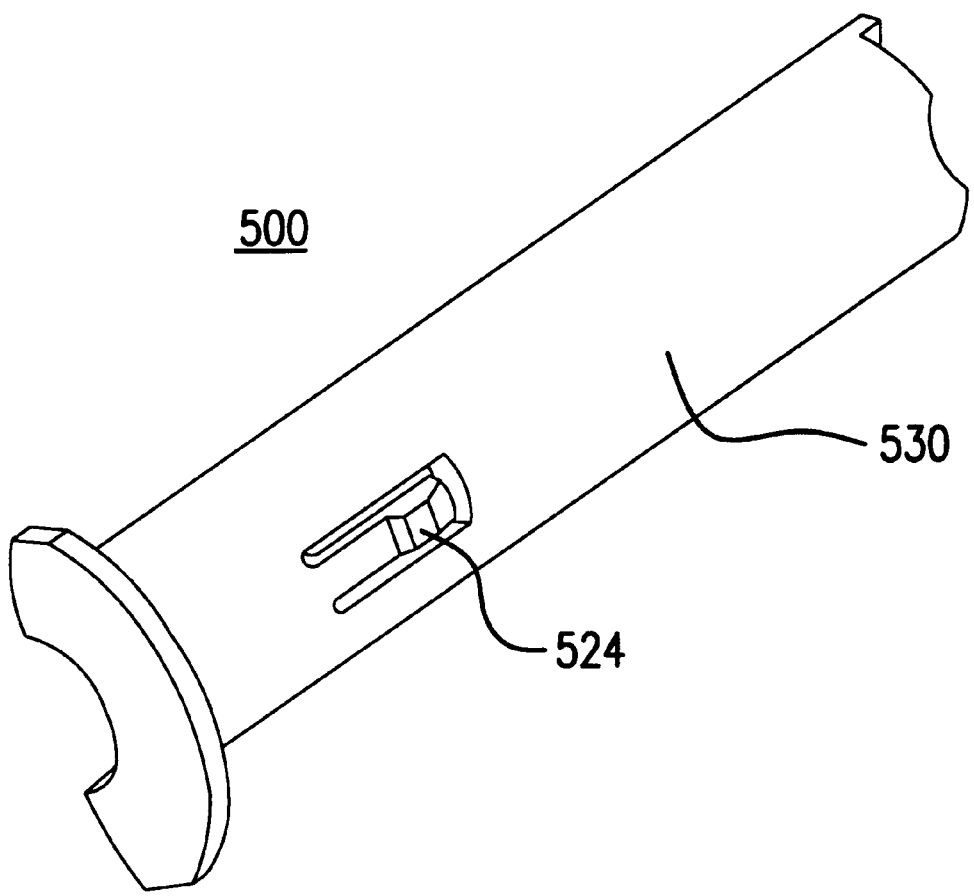
FIG. 26 is a perspective view of the spring holder and deployment catch for the EEG electrode of FIG. 23.
Figure 27:
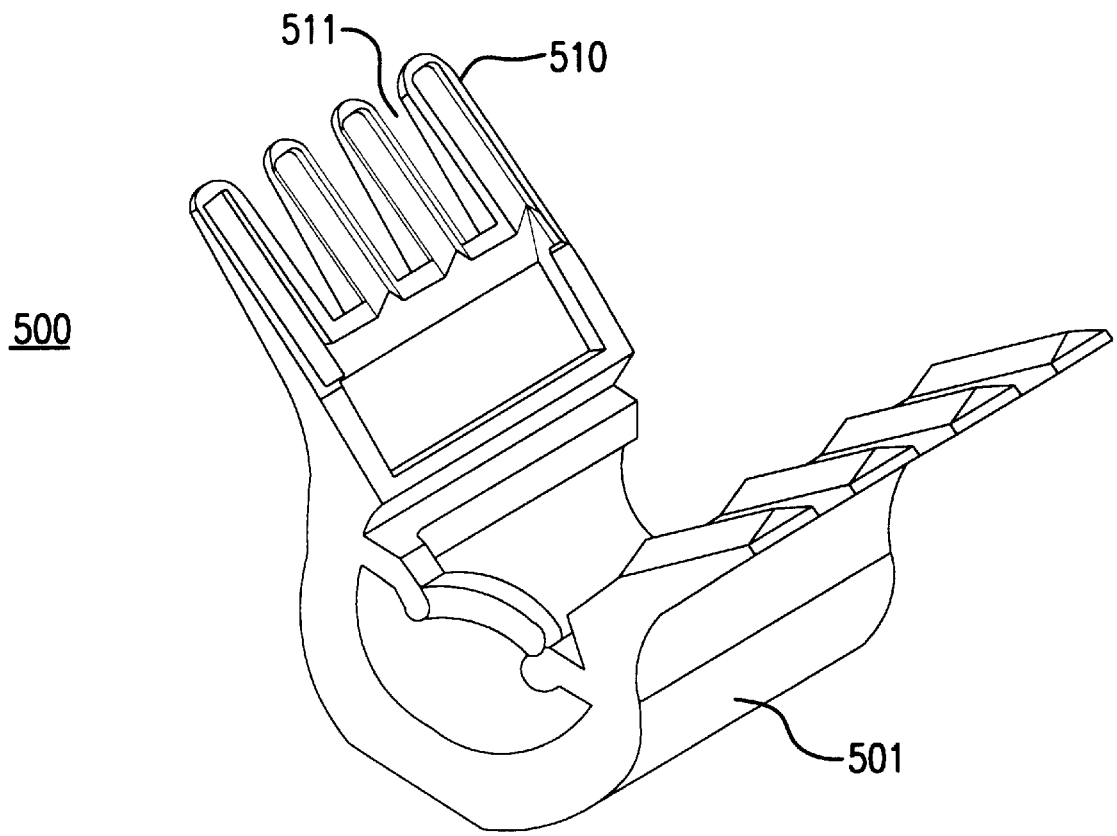
FIG. 27 is a perspective view of the tine set of the EEG electrode of FIG. 23.

Another alternative embodiment for an EEG electrode is shown in FIG. 21. An EEG electrode 400 includes a first element or fixed section, and a second element or movable section that connects to the first element and that operates in conjunction with the first element. In FIG. 21, the first element is shown as a cap 401 with a plurality of serrations 402 and gaps 403 between the serrations 402. The cap 401 also includes locking tabs 407 for a extender unit 430. The second element is shown as a half round extender unit 430. Other configurations for the cap 401 are possible. For example, the cap 401 could have any number of serrations. In addition, affixed to the cap 401 are four, electrolytic gel filled sponges 440.

FIG. 22 shows the extender unit 430 in detail. The extender unit 430 includes two extenders 420, 421, fixably attached to form a half cylinder. Contained within the extender unit 430 is a coil spring 425 affixed to horns 422, 423 on each extender 420, 421. Two locking tabs 424 are located on an exterior of the extenders 420, 421. The extender unit 430 locking grooves 427 on each extender 420, 421 permit the extenders 420 and 421 to mate together to form the half cylinder extender unit 430, and are held in place by the coil spring 425.

The EEG electrode 400 of FIG. 21 may be of small size with a length of about 4 centimeters and a diameter of about 2 centimeters. The cap 401 may be injection molded using acrylonitrile-butadiene styrene (ABS) or similar material. The extenders 420, 421 may be made of a similar material. The coil spring 425 may be made of any spring metal, including stainless steel, for example. The cap 401 and extenders 420, 421 may be made of an electrically conducting plastic or coated with an electrolytic material, for example, as previously described in conjunction with FIG. 3.

In use, the EEG electrode 400 is placed on the patient's scalp and pressed downward where recording is desired, with the cap 401 contacting the scalp. The downward pressure compresses the sponges 440 on the surface of the cap 401 and causes electrolytic gel to be applied to the scalp contact point. Some scalp hairs penetrate the openings 403 between the serrations 402 as well as the openings in the spring 425. The extender unit 430 is then squeezed by applying pressure shown generally by arrows 499, until the locking tabs 424 lock into slots 407. The cap 401 is then pressed towards the patient's scalp until the extenders 420, 421 release from the captured position, releasing the coil spring 425 and thereby clamping the hairs between the coils of the spring 425.

FIGS. 23, 24, 25, 26 and 27 show an alternate embodiment of an EEG electrode 500 having an extender unit and a cap. The extender unit 530 and cap 501 are similar to the extender unit 430 and cap 401 as previously described in conjunction with FIGS. 21 and 22. The EEG electrode 500 is placed against the patient's scalp, and the locking tab 524 is depressed while holding the cap 501 in place. Depressing the locking tab 524 allows the single extender unit 530 to slide along the cap 501, closing an extension spring 525. The patient's hair is captured between coils of the spring 525. The cap 501 and the extender 530 may be coated with an electrolytic material for example, as previously described in conjunction with FIG. 3, or made of electrically conducting plastic.

In yet another embodiment, as shown in FIGS. 28a and 28b, an EEG electrode 700 includes a first element or fixed section, and three second elements or movable sections, that connect to the first element and that operate in conjunction with the first element. In particular, the second elements are movable relative to the first element. The first element is shown as a cover 720 in FIG. 28a, and the second elements are shown as a hair grabbing element 730, a plunger 710, and a sponge 723 with a solid top 740 in FIGS. 29 and 30, respectively.

Referring to FIG. 28b, the cover 720 includes a hollow, cylindrical portion. Also, as will be described later, the cover 720 includes corresponding guide and locking tabs 724 located on an inner wall of the cover 720. The cover 720 also includes a plurality of tube-like protrusions 721 with a hollow passage 722. A sponge 723, saturated with an electrolytic gel 21, and covered by the membrane 22 is encapsulated on the lower rim 726 of the cover 720, and attached to a solid top 740. Using the sponge 723 covered by the membrane 22 ensures that the electrolytic gel 21 will not evaporate during the time that the EEG electrode 700 is attached to the patient's scalp. The sponge 723 may be attached to the EEG electrode 700 immediately prior to use, or may be attached when the EEG electrode 700 is manufactured, for example, as previously described in conjunction with FIG. 3. The sponge 723 and attached solid top 704 can move freely down the hollow tube formed by the cover 720. A bottom 725 of the sponge 723 defines an electrode contact point.

Figure 29:
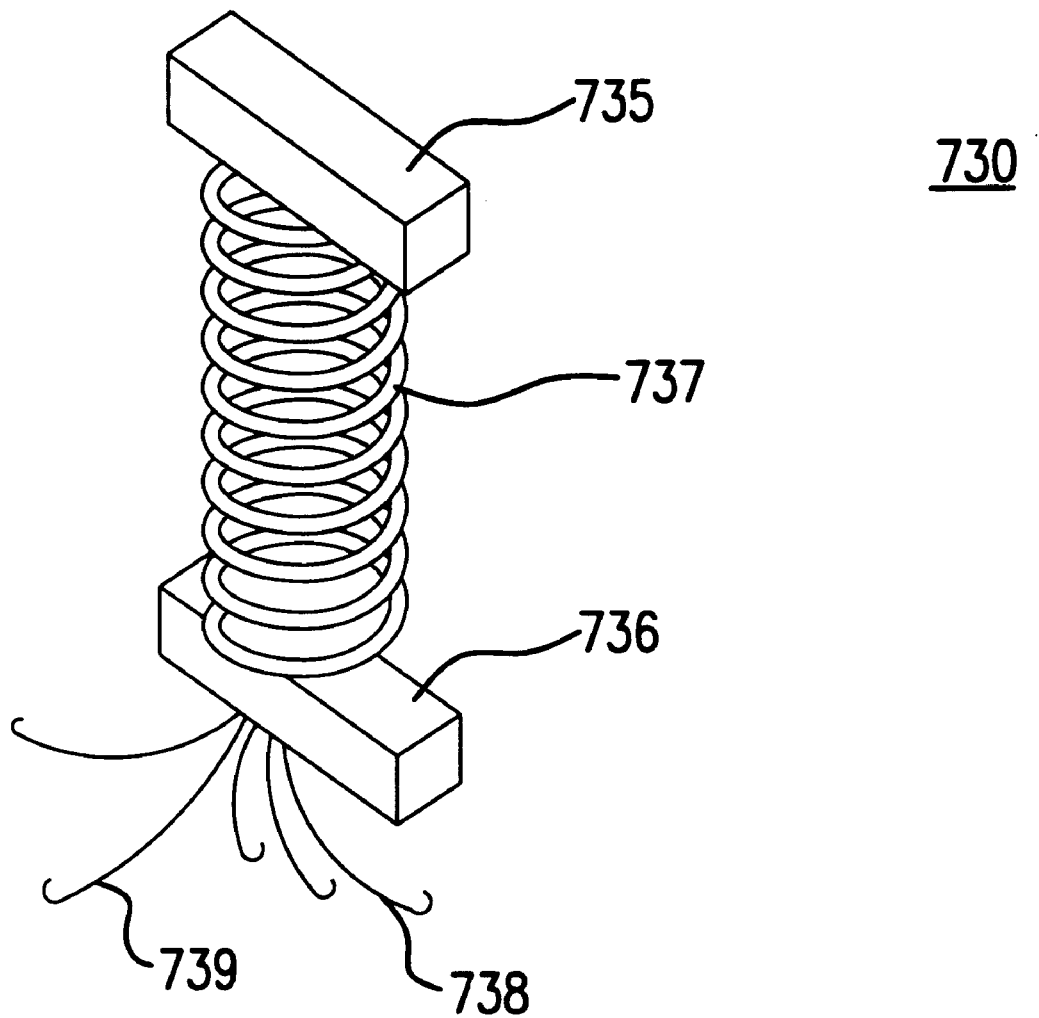
FIG. 29 shows a grabbing element of the EEG electrode of FIGS. 28a and 28b.

Referring to FIG. 29, the grabbing element 730 includes an upper bar 735 and a lower bar 736 fixably attached to each end of a coil spring 737. A length of the upper bar 735 is equal to an inside diameter of the cover 720, and is either physically attached to the inside wall of cover 720 or is fabricated as part of cover 720 as shown in FIG. 28a. The length of the lower bar 736 is greater than a diameter of the plunger, but less than a inside diameter of the cover 720. Attached to the bottom of the lower bar 736 is a tine set 738 including flexible, fish hook shaped wire tines 739 used for grabbing hairs near the scalp.

Figure 30:
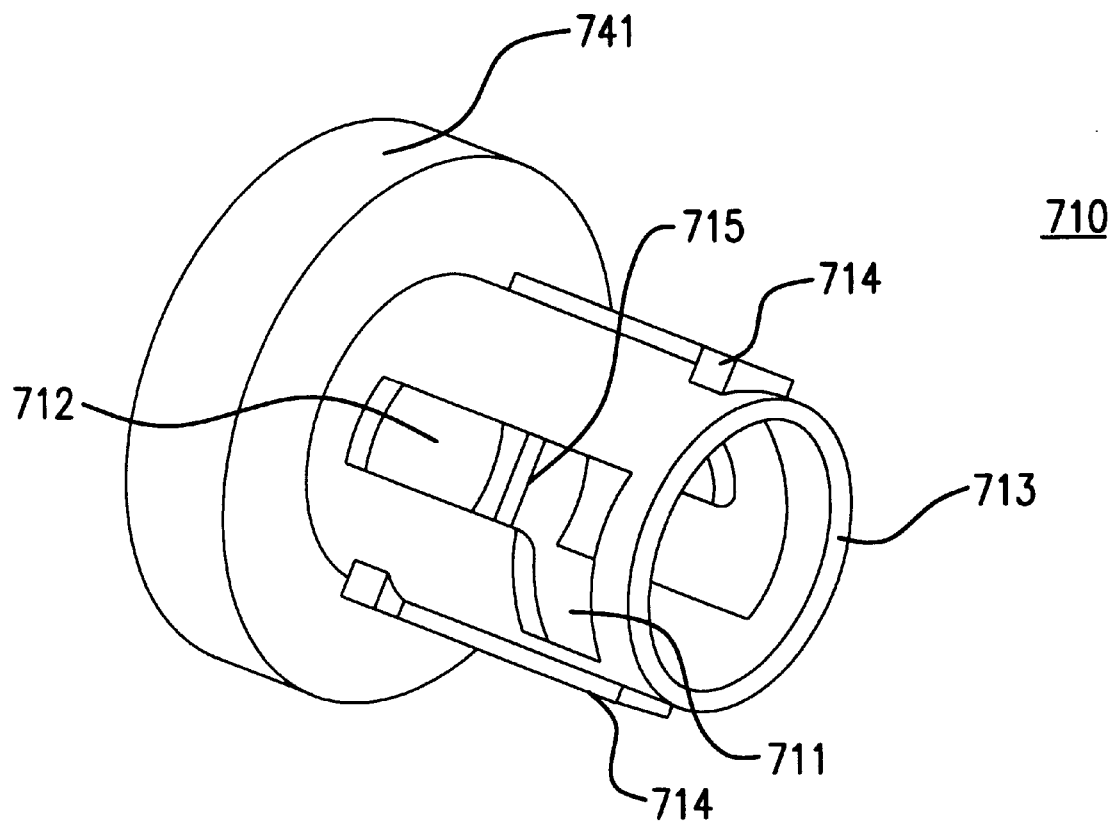
FIG. 30 shows a plunger element of the EEG electrode of FIGS. 28a and 28b.

Referring to FIG. 30, the plunger 710 is a hollow cylinder, with corresponding locking channels 712. As will be described later, the locking channels 712 are used to hold, and then release the coil spring 737 of the grabbing element 730. Also described later, the perturbations 714 are "S" shaped to cause the plunger 710 to rotate within the cover 720 as the plunger 710 is depressed.

The EEG electrode 700 shown in FIG. 28a may be of a small size with a diameter of the cover 720 being about 2 cm, for example. The cover 720 and the solid top 740 may be injection molded using conductive plastic material or a acrylonitrile-butadiene-styrene (ABS) or similar material, and coated with a conductive layer as previously described in conjunction with FIG. 3. The grabbing element 730 may be comprised of similar material and spring steel. The plunger 710 may be injection molded and may be made of a acrylonitrile-butadiene-styrene (ABS) or similar material.

In use, the coil spring 737 is an extension spring that starts non-extended. The grabbing element 730 is aligned within the cover 720 such that the upper bar 735 is attached to the cover 720, passing through the locking channels 712 at approximately one fourth of the way along the length of the locking channels 712 at point 715. The lower bar 736 starts locked in the bottom part 711 of the "L" in the locking channels 712. The plunger 710 is fitted in the cover 720 so that the "S" shaped perturbations 714 of the plunger 710 enter the guide and locking tabs 724 of the cover 720. The individual tines 739 of the tine set 738 are laced through their respective passages 722. Once the grabbing element 730 and plunger 710 are positioned within the cover 720, the individual tines 739 are pulled slightly to partially extend the coil spring 737. The ends of the individual tines are each bent to form a hook, close to the end of the protrusion 721, and then released.

Once a EEG lead wire (not shown) is connected to the EEG electrode 700, the EEG electrode 700 is placed against hair at a point on the patient's scalp where recording is desired, with the bottoms of the protrusions 721 contacting the scalp. When downward pressure is applied to plunger 710, the protrusions 721 flex against the scalp and cause the electrode 700 to move closer to the scalp. The same downward force on the plunger 710 presses against the solid top 740 and causes compression of the sponge 723, as previously described in conjunction with FIG. 3. Depressing the plunger also causes the lower bar 736 to move downward towards the scalp. The upper bar 735 is stationary relative to the cover 720, and the relative movement of the lower bar 736 causes the coil spring 737 to extend. In addition, the downward movement of the lower bar 736 causes the tines 739 to extend through protrusions 721 and out along the scalp. At the halfway point of the downward travel of the plunger 710, the coil spring 737 is fully extended and the "S" shaped curve of the perturbations 714 within the locking grooves 712 of the cover 720 cause the plunger 710 to rotate. The rotation releases the lower bar 736 from the locking portion 711 of the locking channel 712 and allows the spring 737 to retract. The lower bar 736 travels upward, while simultaneously retracting the tines 739. This causes hairs to be captured between the individual tines 739 and the protrusions 721. The plunger 710 continues its downward motion, pushing down on the solid top 740, compressing the sponge 723 against the scalp, whereupon the solid top 740 is forced into the locking mechanism 739 and held in place.

When the pressure on the plunger 710 is released, the compressed sponge 723 provides an upward force raising the electrode 700 above the scalp. This upward motion reduces any slack that may have been present if the hairs were not trapped right next to the scalp. The hair trapped in the grabbing element 730 provides a downward force, thereby creating an equilibrium system. The sponge 723, acting as a shock absorber, maintains constant contact with the scalp, even if the EEG electrode 700 moves up or down in relation to the scalp.

To release the electrode 700, the plunger 710 is pulled upward by the plunger top 741. When the plunger 710 is fully extended, the "S" shaped curve of the perturbations 714 causes the plunger 710 to rotate within the locking grooves 712 of the cover 720, forcing the lower bar 736 to lock itself back into the locking channel 712 at point 711. Then by holding the EEG electrode 700 while simultaneously partially depressing the plunger 710, the tines 739 are extended, and release the trapped hair.

Figure 31:
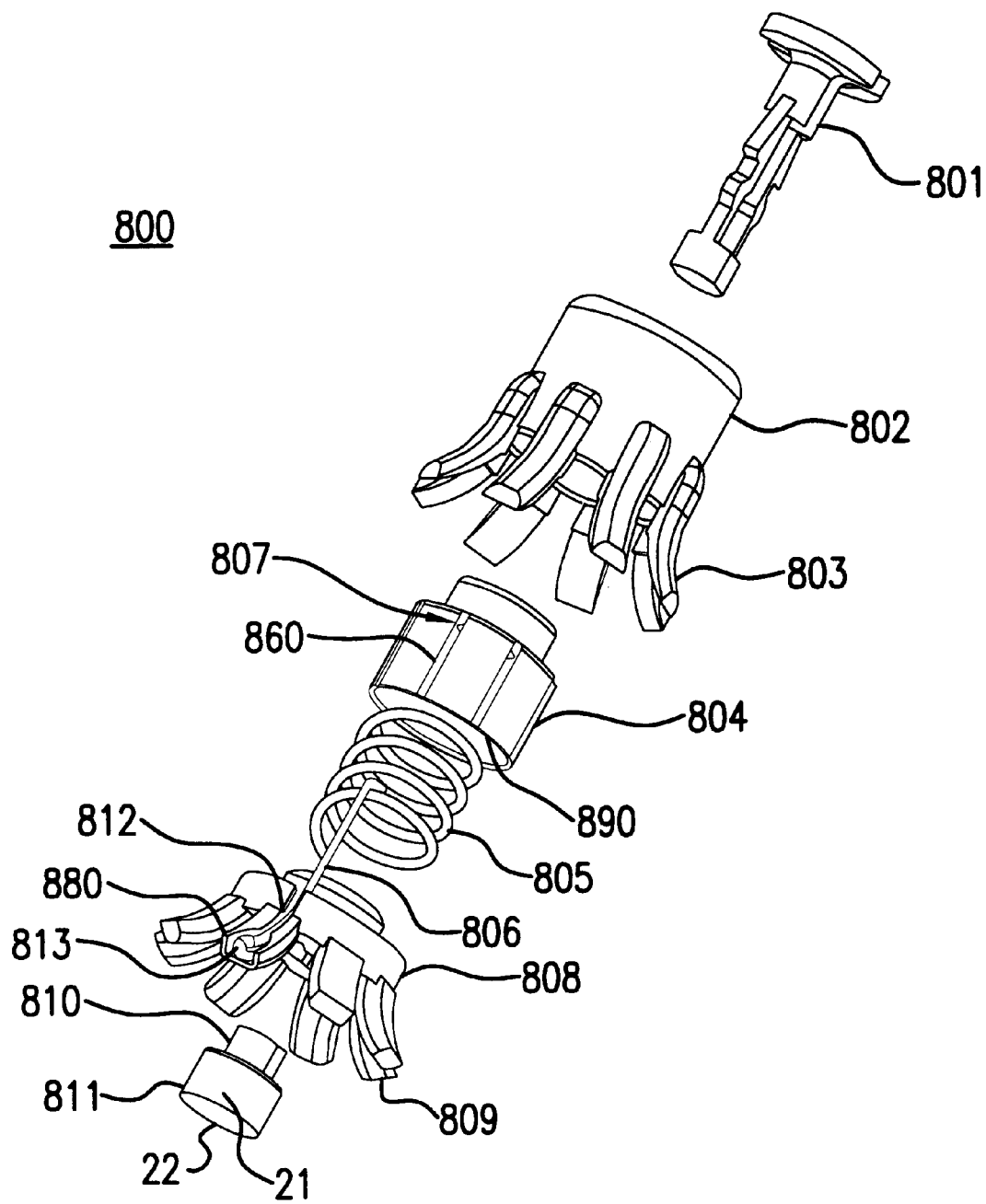
FIG. 31 is the perspective view of a disassembled embodiment of another EEG electrode.

In another embodiment, as shown in FIG. 31, an EEG electrode 800 includes a first element or fixed section, and two second elements or movable sections, that connect to the first element and operate in conjunction with the first element. In particular, the second elements are movable relative to the first element. In FIG. 31, the first element is a housing including a top piece 802 and a bottom piece 808 frictionally fitted together. The second elements are shown as a tine extender 804 and a plunger 801.

Figure 32:
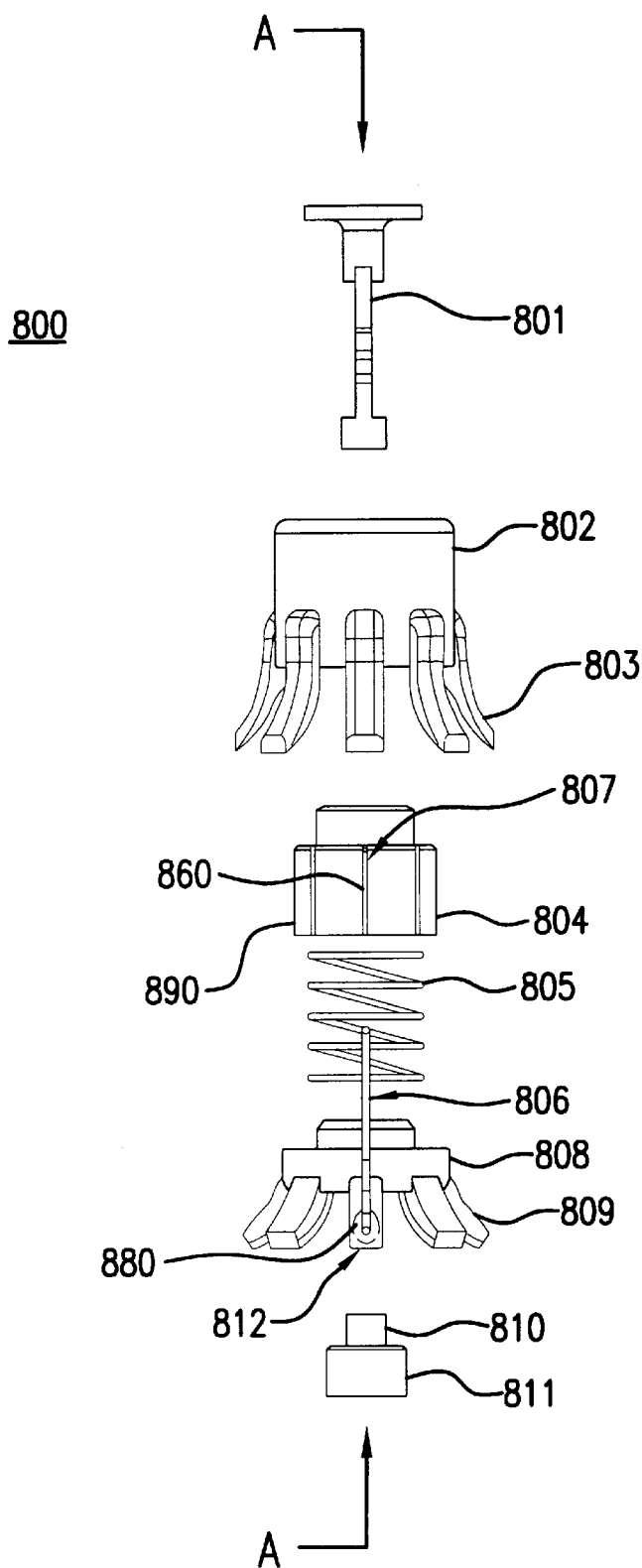
FIG. 32 is the side view of the disassembled EEG electrode of FIG. 31.

Referring to FIGS. 31 and 32, the housing 802, 808, when formed by attaching the top piece 802 and bottom piece 808, includes a hollow, cylindrical portion 890. The hollow, cylindrical portion 890 ends at the bottom piece 808, providing a solid structure to control axial movement of the plunger 801 and the tine extender 804, both of which will be described later. The housing 802, 808 also includes protrusions 803, 809. Each of the protrusions 809 has a hollow passage 812 that leads to a cavity 813.

The plunger 801 can be attached to a solid top 810, which is affixed to a sponge 811 saturated with an electrolytic gel 21, and covered by a membrane 22. The sponge 811 may be attached to the EEG electrode 800 immediately prior to use, or may be attached when the electrode 800 is manufactured, for example, as previously described in conjunction with FIG. 3.

The tine extender 804 houses a compression spring 805. The tine extender 804 also includes tines 806 made of metal, or a similar flexible material, that lock into holes 807. Vertical grooves 860 act as guides for the tines 806. The tines 806 follow the grooves 860 into the hollow passages 812 and then into the cavities 813. Each of the tines 806 forms a hook 880 at a bottom end that fits in the cavity 813.

The EEG electrode 800 shown in FIGS. 31 and 32 may be of a small size with a diameter of the housing 802, 808 being about 2 cm, for example. The housing 802, 808 and the tine extender 804 may be injection molded using acrylonitrile-butadiene-styrene (ABS) or similar material. The plunger 801 and solid top 810 may be constructed from conductive plastic material, or similar material to the housing 802, 808 and tine extender 804 and coated with a conductive layer as previously described in conjunction with FIG. 3. The tines 806 may consist of spring steel or a material similar.

Figure 33:
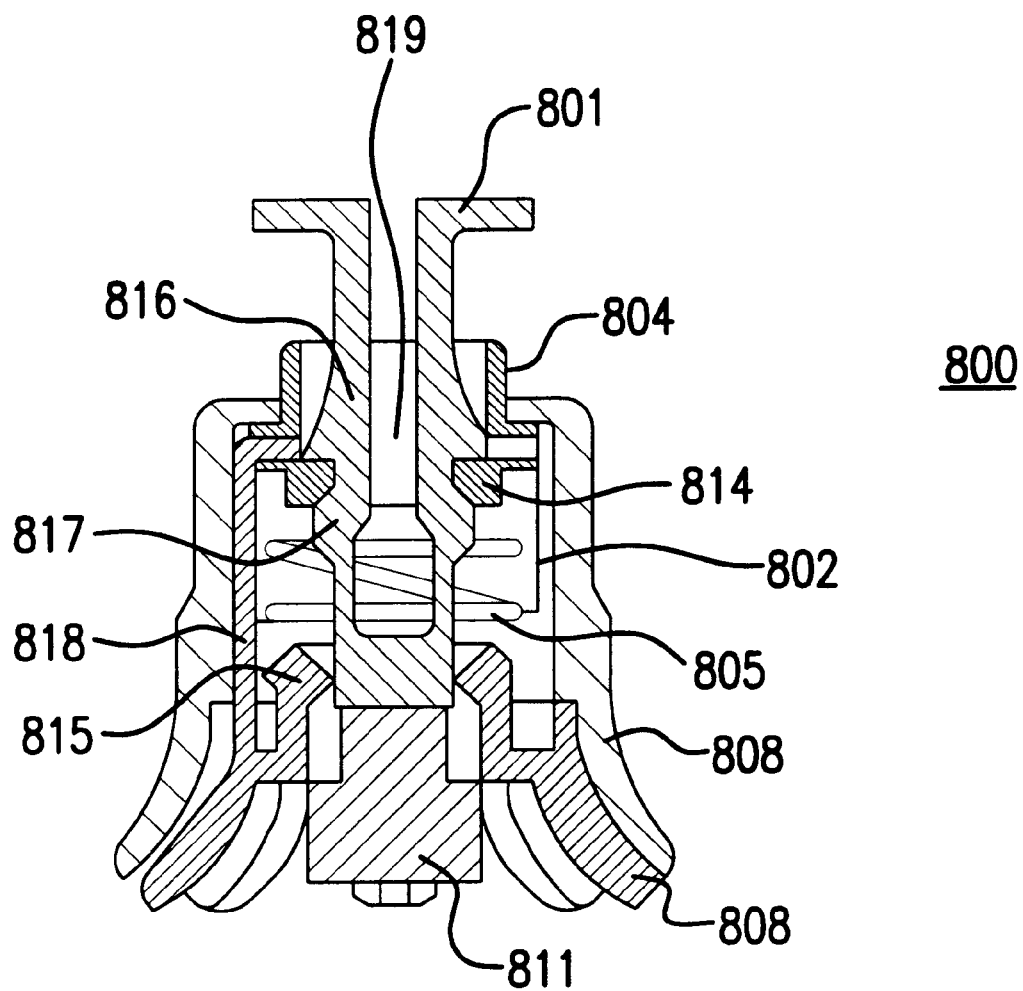
FIG. 33 is a cut-away view of the assembled EEG electrode of FIG. 31.

A cut-away, side view of the electrode 800 as seen in the direction of the arrows A—A of FIG. 32 is presented in FIG. 33, and shows the starting non-deployed configuration of the EEG electrode 800.

Figure 34:
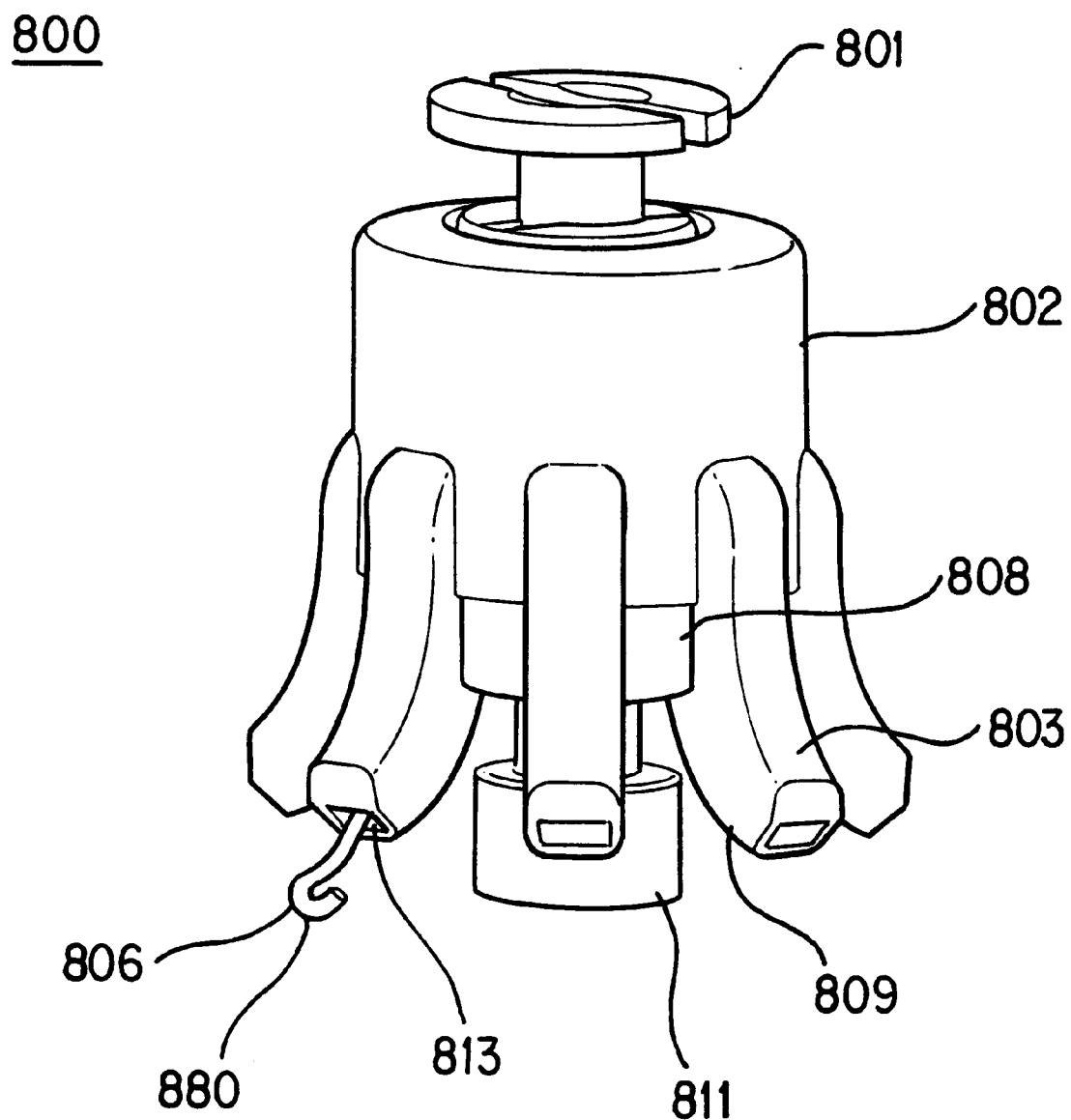
FIG. 34 is a side view of the EEG electrode of FIG. 31 after the plunger is depressed.

In use, the EEG electrode 800 is attached to an EEG lead wire (not shown) and is then placed against the scalp of the patient. Pressure is then applied to the plunger 801. Referring to FIG. 33, the plunger 801 moves towards the scalp, causing an overhang 816 on the plunger 801 to come in contact with a lip 814 on the tine extender 804. The motion of the plunger 801 pushes the tine extender 804 against a coil compression spring 805, causing the tines 806 to extend out of the cavity 813 and flex along the patient's scalp as shown in FIG. 34. Movement of the plunger 801 additionally causes a rapid compression of the sponge 811 in a center of the plunger 801. Operation of the sponge 811 is as previously described in conjunction with FIG. 3.

Figure 35:
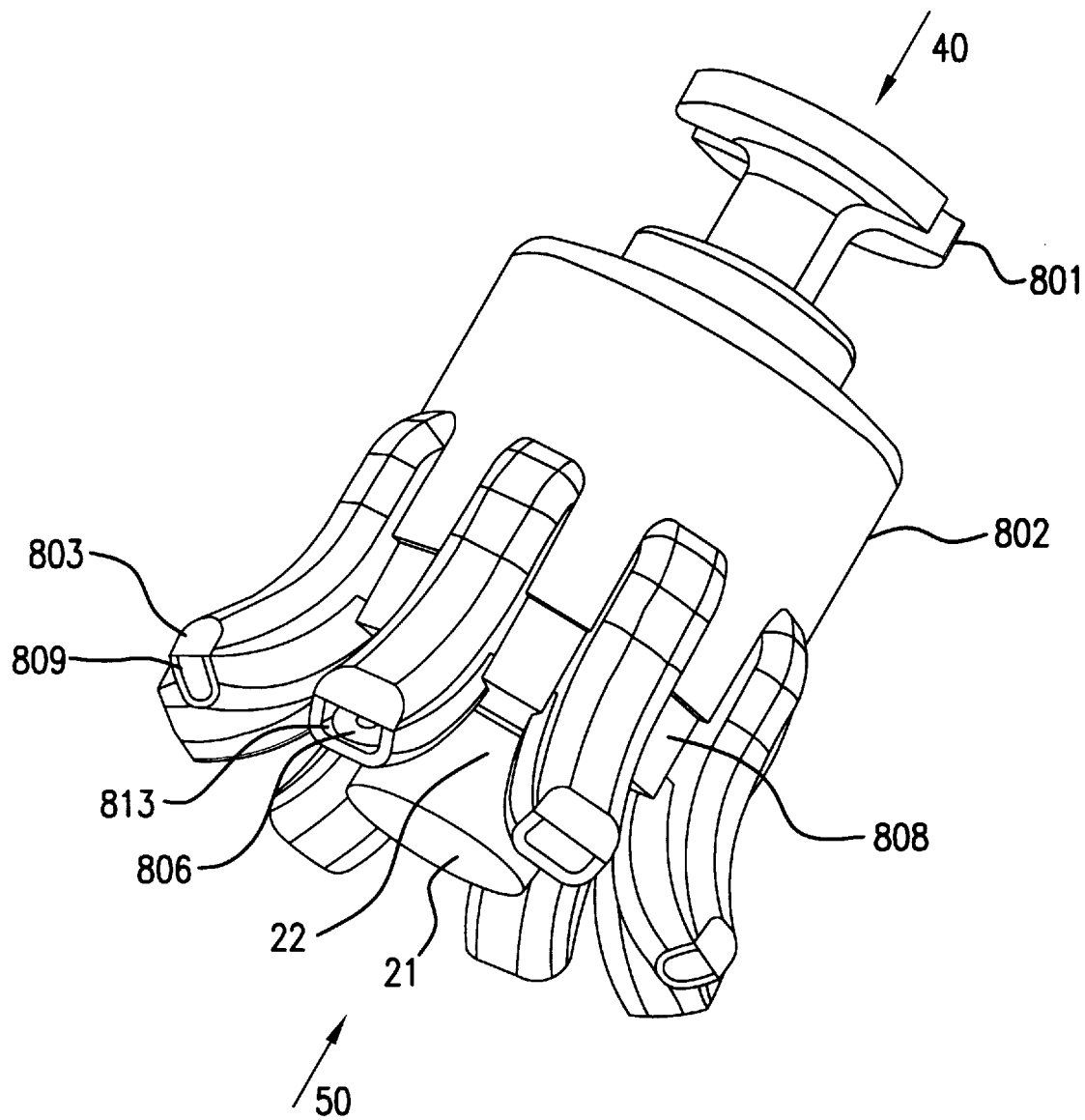
FIG. 35 is a perspective view of the EEG electrode of FIG. 31 after the plunger is fully depressed and the tines have been retracted.

Further depression of the plunger 801 continues deploying the tines 806 and the sponge 811 until the protrusions 817 on the plunger 801 reach the sloped surfaces 815 of the bottom piece 808. The sloped surfaces 815 compresses the protrusions 817 of the plunger 801, forcing the overhang 816 of the plunger 801 to centrally compress. This motion is augmented when the overhang 816 reaches the sloped surfaces 815. This causes the tine extender 804, which experiences a strong upwards force from the compression spring 805, to release from the overhang 816 and come to rest at the top of the housing 802, 808. The upward movement of the tine extender 804 retracts the tines 806, and causes hairs to be trapped by the tines 806. The hairs are then pulled into the cavities 813 in a "U" shape and, the hair is under strong frictional forces and well secured, as shown in FIG. 35. Continued downward pressure, shown generally by arrow 40, on the plunger 801 causes the protrusions 817 of the plunger 801 to pass the sloped surfaces 815, and the sloped surfaces 815 snap into the cavity 819 on the plunger 801, locking the plunger 801 in place.

When pressure on the plunger 801 is released, the compressed sponge 811 provides an upward force, shown generally by arrow 50, raising the electrode 800 above the scalp. This upward motion reduces any slack that may have been present if the hairs were not trapped right next to the scalp. The hair, trapped in the cavities 813 by the tines 806, provides a downward force, shown generally by arrow 40, thereby creating an equilibrium system. The sponge 811, acting as a shock absorber, maintains constant contact with the scalp, even if the EEG electrode 800 moves up or down in relation to the scalp.

To release the electrode 800, the plunger 801 is first compressed and then pulled upward. When the plunger 801 is fully extended, the electrode 800 is held while simultaneously partially depressing the plunger 801. This extends the tines 806 and releases the trapped hair.

While the invention has been described in conjunction with the specific embodiments outlined above, it is evident that many alternatives, modifications and variations will be apparent to those skilled in the art. Accordingly, the preferred embodiments of the invention are intended to be illustrative and not limiting. Various changes may be made without departing from the spirit and scope of the invention as defined in the following claims.

what is claimed:

1. A quick placement electrode for attachment to a patient's scalp, comprising:
    a first element having a central cavity; and
    a second element coupled to the first element and including a hair grabbing element capable of deformation, wherein the hair grabbing element deforms to trap hair, and, wherein a portion of the second element penetrates the central cavity.

2. The quick placement electrode of claim 1, wherein the second element further comprises a plunger having an upper section and a lower section, the upper section extending through the central cavity and capable of vertical movement within the central cavity between an engaged position and a disengaged position, wherein movement of the plunger to the engaged position causes the hair grabbing element to trap hair on the patient's scalp, thereby holding the quick placement electrode in place.

3. The quick placement electrode of claim 2, further comprising:
    a sponge containing an electrolytic gel and connected to the lower section of the plunger; and
    a cover enclosing sides, top and bottom of the sponge, the cover, while intact, preventing the electrolytic gel from leaking from the sponge and from evaporating, wherein downward movement of the plunger compresses the sponge against the patient's scalp, the compression causing a bottom of the covering to rupture thereby applying the electrolytic gel to the patient's scalp.

4. The quick placement electrode of claim 2, further comprising a quick release mechanism.

5. The quick placement electrode of claim 4, wherein the quick release mechanism comprises:
    opposing locking grooves formed by a curved upper ring and a lower ring, the rings molded on the central cavity of the first element;
    opposing break-away ridges formed on the upper section of the plunger and in correspondence with the locking grooves; and
    a stop tab formed on the central cavity of the first element, the stop tab limiting rotation of the plunger in the central cavity, wherein when the quick placement electrode is assembled and the plunger is disengaged, the break-away ridges are aligned with the locking grooves, and wherein when the plunger is engaged, the break-away ridges are captured by the locking grooves.

6. The quick placement electrode of claim 5, wherein when the plunger is engaged and is then further depressed, the break-away ridges shear, the plunger returns to the disengaged position, and the second element releases, thereby permitting removal of the quick placement electrode from the patient's scalp.

7. The quick placement electrode of claim 1, wherein the first element is injection-molded and made from a flexible material including acrylonitrile-butadiene-styrene.

8. The quick placement electrode of claim 1, wherein the second element is injection-molded and made from a flexible material including one of polyurethane and spring steel.

9. The quick placement electrode of claim 1, wherein:
the first element comprises a cap having a lower rim comprising a plurality of serrations; and
the second element comprises a plunger having an upper section and a lower section, the upper section extending through the central cavity and capable of vertical movement within the central cavity between an engaged position and a disengaged position, and wherein the hair grabbing element comprises a tine set coupled to the cap and in communication with the lower section of the plunger and held in place by the connector, the tine set having a plurality of individual tines aligned with corresponding ones of the plurality of serrations, wherein downward motion of the plunger activates the tine set to trap hair on the patient's scalp between the plurality of serrations and the plurality of individual tines, the quick placement electrode held in place by a force created by the activated tine set.

10. The quick placement electrode of claim 9, wherein each of the plurality of individual tines is S-shaped and includes a bottom portion to contact the patient's scalp, and wherein the downward motion of the plunger causes the individual tines to deform thereby changing an orientation of the individual tines such that the individual tines are forced into the serrations.

11. The quick placement electrode of claim 10, wherein when the individual tines deform, the bottom portion rakes along the patient's scalp, parting the hair and forcing the hair into a space between the serrations and the individual tines.

12. The quick placement electrode of claim 9, wherein the tine set is injection-molded and made from a flexible material including polyurethane.

13. The quick placement electrode of claim 9, further comprising:
a sponge containing an electrolytic gel and connected to the lower section of the plunger; and
a cover enclosing sides and a bottom of the sponge, the cover, while intact, preventing the electrolytic gel from leaking from the sponge and from evaporating, wherein downward movement of the plunger compresses the sponge against the patient's scalp, the compression causing a bottom of the covering to rupture thereby applying the electrolytic gel to the patient's scalp.

14. The quick placement electrode of claim 9, further comprising a quick release mechanism, the quick release mechanism comprising:
opposing locking grooves formed by a curved upper ring and a lower ring, the rings molded on the central cavity of the cap;
opposing break-away ridges formed on the upper section of the plunger and in correspondence with the locking grooves; and
a stop tab formed on the central cavity of the cap, the stop tab limiting rotation of the plunger in the central cavity, wherein when the electrode is assembled and the plunger is disengaged, the break-away ridges are aligned with the locking grooves and wherein when the plunger is engaged, the break-away ridges are captured by the locking grooves.

15. The quick placement electrode of claim 9, wherein when the plunger is engaged and is then further depressed, the break-away ridges shear, the plunger returns to the disengaged position, and the flexible tines relax thereby permitting removal of the quick placement electrode from the scalp of the patient.

16. The quick placement electrode of claim 9, wherein the serrations are arcuate and the individual tines are hemispherical in cross-section, the hemispherical shape conforming generally to the arcuate serrations.

17. The quick placement electrode of claim 1, wherein:
the first element comprises a cap having the central cavity; and
the second element comprises a tine set, coupled to the cap, the tine set having a plurality of individual tines, wherein downward motion of the cap activates the tine set to trap hair on the patient's scalp between the plurality of tines, the electrode held on place by a force created by the activated tine set.

18. The quick placement electrode of claim 1, wherein:
the first element comprises a cap having the central cavity, the cap having a plurality of ridges within the central cavity; and
the second element comprises a coil spring capable of rotation, the coil spring comprising a plurality of winds and having an upper section and a lower section, the upper section extending through the central cavity and capable of vertical movement within the central cavity between an engaged position and a disengaged position, wherein the coil spring is rotated and downward motion of the cap compresses the coil spring to trap hair on the patient's scalp between the plurality of winds in the coil spring and the cap, the electrode being held in place by a force created by the coil spring.

19. The quick placement electrode of claim 1, further comprising:
the first element having a fixed section, the fixed section comprising serrations located on a bottom perimeter of the fixed section; and
the second element comprising a movable section, the movable section connected to an underside of the fixed section and having flexible tines aligned with the serrations, wherein when a downward force is applied to the movable section, the flexible tines trap hair between the flexible tines and the serrations.

20. The electrode of claim 19, wherein the second element further comprises:
a plunger; and
a tine set having a center, the tine set connected to the plunger and to the flexible tines, wherein the plunger penetrates the central cavity and connects with the center of the tine set, and wherein when the downward force is applied to the movable section, the plunger presses on the center of the tine set causing the tine set to pivot about the connections and the flexible tines to reorient, thereby trapping the hair between the flexible tines and the serrations.

21. The electrode of claim 19, wherein the second element comprises a single movable piece, the single movable piece, including:
a plunger section; and
a tine set formed continuously with the plunger section and the flexible tines, wherein a top of the plunger section penetrates the central cavity, and wherein when the downward force is applied to the movable section, the tine set pivots about the connections, thereby trapping hair between the flexible tines and the serrations.

22. The electrode of claim 20, wherein when the downward force is applied to the movable section, and the tine set pivots, the flexible tines reorient to trap the hair.

23. An electroencephalogram (EEG) electrode, comprising:
- a first element having a cavity; and
- a second element connected to the first element, the second element comprising:
  - a tine set having flexible tines projecting therefrom, and
  - a plunger connected to the tine set and operable to cause the flexible tines to reorient so as to trap hair between the flexible tines and the first element, and having an upper center section through which a sponge may be passed and a lower center section that holds the sponge.

24. The EEG electrode assembly of claim 23, wherein the first element includes serrations along a lower perimeter of the first element, and wherein the tine set is aligned with the serrations so that when the flexible tines reorient, the flexible tines trap the hair between the flexible tines and void portions of the serrations.

25. The EEG electrode of claim 23, further comprising:
- a sponge containing an electrolytic gel and connected within the cavity; and
- a cover enclosing sides and a bottom of the sponge, the cover, while intact, preventing the electrolytic gel from leaking from the sponge and from evaporating, wherein downward movement of the plunger compresses the sponge against the patient's scalp, the compression causing a bottom of the covering to rupture thereby applying the electrolytic gel to the patient's scalp.

26. The EEG electrode of claim 23, wherein each of the plurality of individual tines includes a bottom portion to contact the patient's scalp, and wherein the downward motion of the plunger causes the flexible tines to deform thereby changing an orientation of the flexible tine.

27. The EEG electrode of claim 26, wherein when the flexible tines deform, the bottom portion rakes along the patient's scalp, parting the hair and forcing the hair into a space between the flexible tines.

28. The EEG electrode of claim 26, wherein the tine set is one of spring steel and polyurethane.

29. A quick placement electrode for attachment to a patient's scalp, comprising:
- a cap; and
- a tine set, coupled to the cap, the tine set having a plurality of individual tines, wherein downward motion of the cap activates the tine set to trap hair on the patient's scalp between the plurality of individual tines, the electrode held in place by a force created by the activated tine set.

30. The quick placement electrode of claim 29, further comprising:
- the cap having a central cavity and a connector;
- a sponge containing an electrolytic gel and connected within the central cavity; and
- a cover enclosing sides and a bottom of the sponge, the cover, while intact, preventing the electrolytic gel from leaking from the sponge and from evaporating, wherein downward movement of the cap compresses the sponge against the patient's scalp, the compression causing a bottom of the covering to rupture thereby applying the electrolytic gel to the patient's scalp.

31. The quick placement electrode of claim 29, wherein each of the plurality of individual tines includes a bottom portion to contact the patient's scalp, and wherein the downward motion of the cap causes the individual tines to deform thereby changing an orientation of the individual tines.

32. The quick placement electrode of claim 29, wherein when the individual tines deform, the bottom portion rakes along the patient's scalp, parting the hair and forcing the hair into a space between the individual tines.

33. The quick placement electrode of claim 29, wherein the tine set is made of one of spring steel and polyurethane.

34. A quick placement electrode for attachment to a patient's scalp, comprising:
- a cap having a central cavity and having a plurality of ridges within the central cavity; and
- a coil spring having an upper section and a lower section, the upper section extending through the central cavity and capable of vertical movement within the central cavity between an engaged position and a disengaged position, wherein the coil spring is rotated and downward motion of the cap compresses the coil spring to trap hair on the patient's scalp between a plurality of winds in the coil spring and the cap, the electrode being held in place by a force created by the coil spring.

35. The quick placement electrode of claim 34, further comprising:
- a sponge containing an electrolytic gel and connected within the interior of the spring; and
- a cover enclosing sides and a bottom of the sponge, the cover, while intact, preventing the electrolytic gel from leaking from the sponge and from evaporating, wherein downward movement of the cap compresses the sponge against the patient's scalp, the compression causing a bottom of the covering to rupture thereby applying the electrolytic gel to the patient's scalp.

36. A method for using an electroencephalogram (EEG) electrode, comprising:
- placing the EEG electrode at a scalp placement point, wherein the EEG electrode comprises a first element and a second element, the second element including a flexible grabbing element connected to the second element, the second element coupled to the first element; and
- depressing the first element to deform the flexible grabbing element trap hair and to hold the EEG electrode in place on a patient's scalp, wherein the hair is trapped between the first and second elements.

37. The method of claim 36, further comprising:
- pressing the first element to deactivate the second element, thereby freeing the trapped hair; and
- removing the EEG electrode from the patient's scalp.

38. A method for using an electroencephalogram (EGG) electrode, comprising:
- placing the EEG electrode at a scalp placement point, wherein the EEG electrode comprises a first element and a second element, the second element including a hair grabbing element, the second element coupled to the first element, and wherein the second element includes a sponge containing electrolytic gel;
- depressing the first element to dispense the electrolytic gel and trap hair to hold the EEG electrode in place on a patient's scalp, wherein the hair is trapped between the first element and the second element; and
- monitoring signals from the EEG electrode.

39. The method of claim 38, further comprising:
- when EEG monitoring is complete, further pressing the first element to deactivate the second element, thereby freeing the trapped hair; and
- removing the EEG electrode from the patient's scalp.

40. A method for using an EGG electrode, comprising:

placing the EEG electrode at a scalp placement point, wherein the EEG electrode comprises a first element and a second element, the second element including a plunger and a grabbing element connected to the plunger, the second element coupled to the first element, and wherein the plunger includes a sponge containing electrolytic gel;

depressing the plunger to dispense the electrolytic gel and trap hair to hold the EEG electrode in place on a patient's scalp, wherein the hair is trapped between the first and second elements; and monitoring signals from the EEG electrode.

41. The method of claim 40, further comprising:

when EEG monitoring is complete, further pressing the plunger to activate a quick-release mechanism, thereby freeing the trapped hair; and removing the EEG electrode from the patient's scalp.

42. The method of claim 40, wherein the quick-release mechanism includes a locking groove and locking ring, and wherein first depressing the plunger causes the locking ring to engage the locking groove thereby holding the plunger in an engaged position and further pressing the plunger releases the locking ring to return the plunger to a disengaged position.

43. A quick placement electrode for placement on a patient's scalp, comprising:

a housing, comprising:
  a sponge that contacts the patient's scalp, and
  a plurality of protrusions, ends of the plurality of protrusions contacting the patient's scalp; and a movable part connected to the housing and movable with respect to the housing, the movable part in cooperation with the housing capable of trapping hair on the patient's scalp to hold the quick placement electrode in place on the patient's scalp.

44. The quick placement electrode of claim 43, wherein the housing further comprises a hollow cylindrical section and an inner wall, the inner wall including a guide and lock tab assembly and wherein a protrusion comprises a hollow passage.

45. The quick placement electrode of claim 44, further comprising:

a plunger comprising:
  a hollow cylinder having slots formed in a cylinder wall,
  an end cap attached to an upper end of the plunger, and
  guide bars formed on an outside surface of the cylinder wall, wherein an outside diameter of the plunger hollow cylinder is less than an inside diameter of the housing; and a grabbing element, comprising:
  an upper bar fixedly attached to the inner wall of the housing,
  a lower bar,
  a spring attached between the upper bar and the lower bar, wherein a length of the lower bar is greater than the outside diameter of the plunger and less than the inside diameter of the housing, and
  flexible tines having hooks formed on end portions, wherein a flexible tine passes through each of the plurality the hollow protrusions, a hook extending beyond an end of the hollow protrusion, wherein a first operation of the plunger extends the tines, and a second operation of the plunger causes retraction of the tines, thereby trapping hair in the hooks.

\* \* \* \* \*